US008053635B2

(12) United States Patent
Kok-Jacon et al.

(10) Patent No.: US 8,053,635 B2
(45) Date of Patent: Nov. 8, 2011

(54) TRANSFORMED PLANT EXPRESSING A DEXTRANSUCRASE AND SYNTHESIZING A MODIFIED STARCH

(75) Inventors: Geraldine Kok-Jacon, Hamme-Mille (BE); Jean-Paul Vincken, Renkum (NL); Luc C J M Suurs, Zetten (NL); Claus Frohberg, Kleinmachnow (DE); Richard G F Visser, Bennekom (NL)

(73) Assignee: Bayer CropScience AG, Monheim AM Rhein (DE)

( * ) Notice: Subject to any disclaimer, the term of this patent is extended or adjusted under 35 U.S.C. 154(b) by 768 days.

(21) Appl. No.: 11/793,263

(22) PCT Filed: Dec. 19, 2005

(86) PCT No.: PCT/EP2005/013954
§ 371 (c)(1),
(2), (4) Date: May 30, 2008

(87) PCT Pub. No.: WO2006/063862
PCT Pub. Date: Jun. 22, 2006

(65) Prior Publication Data
US 2009/0064372 A1    Mar. 5, 2009

Related U.S. Application Data

(60) Provisional application No. 60/637,900, filed on Dec. 21, 2004.

(30) Foreign Application Priority Data

Dec. 17, 2004  (EP) .................................... 04029934

(51) Int. Cl.
*C12N 15/82* (2006.01)
*C12N 15/09* (2006.01)
*C12N 15/31* (2006.01)
*C12N 15/00* (2006.01)
*A01H 5/00* (2006.01)
*A01H 5/10* (2006.01)

(52) U.S. Cl. ..................... 800/284; 800/278; 435/320.1; 435/468; 536/23.1; 536/23.7; 536/23.2

(58) Field of Classification Search ........................ None
See application file for complete search history.

(56) References Cited

U.S. PATENT DOCUMENTS
6,833,491 B2 * 12/2004 Turk et al. ..................... 800/284

FOREIGN PATENT DOCUMENTS
| JP | 2003-111590 | 4/2003 |
| WO | WO 89/12386 | 12/1989 |
| WO | WO8912386 | * 12/1989 |
| WO | WO 95/13389 | 5/1995 |
| WO | WO 00/47727 | 8/2000 |
| WO | WO 2004/099403 | 11/2004 |

OTHER PUBLICATIONS

Anonymous "Research Projects 2002, Laboratory of Plant Breeding, Wageningen University and Research Centre." Retrieved from the internet on Nov. 5, 2005.
Gerrits, et al. (Feb. 2001) "Sucrose metabolism in plastids." Plant Physiology 12592): 926-934.
Ji, et al. (Mar. 2003) "Microbial starch-binding domains as a tool for targeting proteins to granules during starch biosynthesis." Plant Molecular Biology 51(5): 789-801.
Kok-Jacon, et al. (Jul. 2003) "Towards a more Versatile Alpha-Glucan Biosynthesis in Plants." Journal of Plant Physiology 160(7): 765-777.
Machine Translation of JP 2003-111590, listed at Cite No. 1.

* cited by examiner

*Primary Examiner* — Brent T Page
(74) *Attorney, Agent, or Firm* — Hunton & Williams LLP

(57) ABSTRACT

The present invention relates to plant cells and plants, which are genetically modified, wherein the genetic modification leads to the expression in plastids of such plant cells and plants of an enzyme having the activity of a dextransucrase. Furthermore, the present invention relates to means and methods for the manufacture of such plant cells and plants. Plant cells and plants of this type synthesis a modified starch. The present invention therefore also relates to the starch synthesized by the plant cells and plants according to the invention as well as to methods for the manufacture of the starch and to the manufacture of starch derivatives of this modified starch.

41 Claims, 2 Drawing Sheets

Kardal

DsrS 30

SEQUENCE LISTING

<160> NUMBER OF SEQ ID NOS: 6

<210> SEQ ID NO 1
<211> LENGTH: 4584
<212> TYPE: DNA
<213> ORGANISM: Leuconostoc mesenteroides
<220> FEATURE:
<221> NAME/KEY: CDS
<222> LOCATION: (1)..(4584)
<223> OTHER INFORMATION: complete CDS

<400> SEQUENCE: 1

```
atg cca ttt aca gaa aaa gta atg cgg aaa aag ctt tat aaa gtt ggg      48
Met Pro Phe Thr Glu Lys Val Met Arg Lys Lys Leu Tyr Lys Val Gly
1               5                   10                  15 aaa agt tgg gta gtt ggt ggg gtt tgt gct ttt gca tta acc gcc tca      96
Lys Ser Trp Val Val Gly Gly Val Cys Ala Phe Ala Leu Thr Ala Ser
            20                  25                  30 ttt gct tta gca aca cca agt gtt tta gga gac agt agt gta cct gat     144
Phe Ala Leu Ala Thr Pro Ser Val Leu Gly Asp Ser Ser Val Pro Asp
        35                  40                  45 gtg agt gcg aat aac gtt caa tct gct tca gat aat aca acg gat acg     192
Val Ser Ala Asn Asn Val Gln Ser Ala Ser Asp Asn Thr Thr Asp Thr
    50                  55                  60 cag cag aac act acg gtt acc gaa gaa aat gat aaa gta cag tct gca     240
Gln Gln Asn Thr Thr Val Thr Glu Glu Asn Asp Lys Val Gln Ser Ala
65                  70                  75                  80 gct act aat gac aat gta aca aca gct gca agc gac aca caa tct         288
Ala Thr Asn Asp Asn Val Thr Thr Ala Ala Ser Asp Thr Thr Gln Ser
                85                  90                  95 gct gat aat aat gtg aca gaa aaa cag tca gat gat cat gca ctt gat     336
Ala Asp Asn Asn Val Thr Glu Lys Gln Ser Asp Asp His Ala Leu Asp
            100                 105                 110 aat gaa aaa gtc gat aac aaa caa gat gaa gtc gct caa acc aat gtt     384
Asn Glu Lys Val Asp Asn Lys Gln Asp Glu Val Ala Gln Thr Asn Val
        115                 120                 125 act agc aaa aat gag gaa tca gca gtt gct tca act gac act gat cct     432
Thr Ser Lys Asn Glu Glu Ser Ala Val Ala Ser Thr Asp Thr Asp Pro
    130                 135                 140 gct gaa acg aca act gac gaa aca caa caa gtt agc ggc aag tac gtt     480
Ala Glu Thr Thr Thr Asp Glu Thr Gln Gln Val Ser Gly Lys Tyr Val
145                 150                 155                 160 gaa aaa gac ggt agt tgg tat tat tat ttt gat gat ggc aaa aat gct     528
Glu Lys Asp Gly Ser Trp Tyr Tyr Tyr Phe Asp Asp Gly Lys Asn Ala
                165                 170                 175 aaa ggt tta tca acg ata gac aac aat att caa tat ttt tac gag agt     576
Lys Gly Leu Ser Thr Ile Asp Asn Asn Ile Gln Tyr Phe Tyr Glu Ser
            180                 185                 190 ggt aaa caa gcc aaa gga cag tat gtc aca att gat aat caa aca tat     624
Gly Lys Gln Ala Lys Gly Gln Tyr Val Thr Ile Asp Asn Gln Thr Tyr
        195                 200                 205 tat ttt gat aag ggc tca ggt gat gag tta act ggt ctg caa agc att     672
Tyr Phe Asp Lys Gly Ser Gly Asp Glu Leu Thr Gly Leu Gln Ser Ile
    210                 215                 220 gat ggg aac ata gtt gct ttt aac gat gaa ggg caa caa att ttt aat     720
Asp Gly Asn Ile Val Ala Phe Asn Asp Glu Gly Gln Gln Ile Phe Asn
225                 230                 235                 240 caa tat tac caa tct gaa aat ggt aca aca tac tac ttt gat gat aaa     768
Gln Tyr Tyr Gln Ser Glu Asn Gly Thr Thr Tyr Tyr Phe Asp Asp Lys
                245                 250                 255
```

```
gga cac gct gct acc ggt att aag aat atc gag ggc aaa aat tat tat         816
Gly His Ala Ala Thr Gly Ile Lys Asn Ile Glu Gly Lys Asn Tyr Tyr
        260                 265                 270 ttt gat aat ctt ggg caa cta aaa aaa ggc ttc tct ggt gtg att gat         864
Phe Asp Asn Leu Gly Gln Leu Lys Lys Gly Phe Ser Gly Val Ile Asp
275                 280                 285 ggt caa ata atg aca ttt gat cag gaa aca ggg caa gaa gtt tct aac         912
Gly Gln Ile Met Thr Phe Asp Gln Glu Thr Gly Gln Glu Val Ser Asn
        290                 295                 300 aca act tct gaa ata aaa gaa ggt ttg acg act caa aac acg gat tat         960
Thr Thr Ser Glu Ile Lys Glu Gly Leu Thr Thr Gln Asn Thr Asp Tyr
305                 310                 315                 320 agc gaa cat aat gca gcc cac ggt acg gat gct gag gac ttt gaa aat        1008
Ser Glu His Asn Ala Ala His Gly Thr Asp Ala Glu Asp Phe Glu Asn
                325                 330                 335 att gac ggc tat tta aca gct agt tca tgg tat cgt cca aca ggt att        1056
Ile Asp Gly Tyr Leu Thr Ala Ser Ser Trp Tyr Arg Pro Thr Gly Ile
            340                 345                 350 tta cgt aac gga aca gac tgg gaa cct tct aca gat aca gat ttc aga        1104
Leu Arg Asn Gly Thr Asp Trp Glu Pro Ser Thr Asp Thr Asp Phe Arg
        355                 360                 365 cca ata ttg tca gtg tgg tgg cca gat aag aac acc cag gtc aat tat        1152
Pro Ile Leu Ser Val Trp Trp Pro Asp Lys Asn Thr Gln Val Asn Tyr
370                 375                 380 tta aat tac atg gct gat tta ggg ttt atc agt aat gcg gac agt ttt        1200
Leu Asn Tyr Met Ala Asp Leu Gly Phe Ile Ser Asn Ala Asp Ser Phe
385                 390                 395                 400 gaa act ggg gat agc caa agc tta tta aat gaa gca agt aac tat gtt        1248
Glu Thr Gly Asp Ser Gln Ser Leu Leu Asn Glu Ala Ser Asn Tyr Val
                405                 410                 415 caa aaa tca att gaa atg aaa att agt gcg caa caa agt aca gag tgg        1296
Gln Lys Ser Ile Glu Met Lys Ile Ser Ala Gln Gln Ser Thr Glu Trp
            420                 425                 430 tta aag gat gca atg gcg gcc ttc att gtc gcg caa cca cag tgg aat        1344
Leu Lys Asp Ala Met Ala Ala Phe Ile Val Ala Gln Pro Gln Trp Asn
        435                 440                 445 gaa act agt gaa gat atg agc aat gac cat tta caa aat ggc gca tta        1392
Glu Thr Ser Glu Asp Met Ser Asn Asp His Leu Gln Asn Gly Ala Leu
450                 455                 460 act tat gtc aac agt cca ctg aca cct gac gct aat tca aac ttt aga        1440
Thr Tyr Val Asn Ser Pro Leu Thr Pro Asp Ala Asn Ser Asn Phe Arg
465                 470                 475                 480 cta ctt aat cgg aca cca aca aac cag act ggt gaa caa gcg tat aat        1488
Leu Leu Asn Arg Thr Pro Thr Asn Gln Thr Gly Glu Gln Ala Tyr Asn
                485                 490                 495 tta gat aat tca aaa ggt ggt ttt gaa ttg ttg tta gcc aat cag gaa        1536
Leu Asp Asn Ser Lys Gly Gly Phe Glu Leu Leu Leu Ala Asn Gln Glu
            500                 505                 510 gat aat tca aac gtt gta gta gaa gca gaa caa ttg aat tgg tta tat        1584
Asp Asn Ser Asn Val Val Val Glu Ala Glu Gln Leu Asn Trp Leu Tyr
        515                 520                 525 tat tta atg aat ttt ggt acg att acg gcc aac gac gcg gat gct aat        1632
Tyr Leu Met Asn Phe Gly Thr Ile Thr Ala Asn Asp Ala Asp Ala Asn
530                 535                 540 ttt gat ggt att cgt gta gat gca gtc gac aat gtg gat gct gat ttg        1680
Phe Asp Gly Ile Arg Val Asp Ala Val Asp Asn Val Asp Ala Asp Leu
545                 550                 555                 560 tta caa att gct gcc gat tat ttc aaa cta gct tac ggt gtt gat caa        1728
Leu Gln Ile Ala Ala Asp Tyr Phe Lys Leu Ala Tyr Gly Val Asp Gln
                565                 570                 575
```

-continued

| | |
|---|---|
| aat gat gct act gct aat cag cat ctt tca att ttg gaa gat tgg agt<br>Asn Asp Ala Thr Ala Asn Gln His Leu Ser Ile Leu Glu Asp Trp Ser<br>580 585 590 | 1776 |
| cac aat gat cct ttg tat gta aca gat caa gga agc aat caa tta acc<br>His Asn Asp Pro Leu Tyr Val Thr Asp Gln Gly Ser Asn Gln Leu Thr<br>595 600 605 | 1824 |
| atg gat gat tat gtg cac aca caa tta atc tgg tct cta aca aaa tca<br>Met Asp Asp Tyr Val His Thr Gln Leu Ile Trp Ser Leu Thr Lys Ser<br>610 615 620 | 1872 |
| tct gac ata cga ggt aca atg cag cgc ttc gtg gat tat tat atg gtg<br>Ser Asp Ile Arg Gly Thr Met Gln Arg Phe Val Asp Tyr Tyr Met Val<br>625 630 635 640 | 1920 |
| gat cga tct aat gat agt aca gaa aac gaa gcc att cct aat tac agc<br>Asp Arg Ser Asn Asp Ser Thr Glu Asn Glu Ala Ile Pro Asn Tyr Ser<br>645 650 655 | 1968 |
| ttt gta cgt gca cac gac agc gaa gtg caa acg gtt att gcc caa att<br>Phe Val Arg Ala His Asp Ser Glu Val Gln Thr Val Ile Ala Gln Ile<br>660 665 670 | 2016 |
| gtt tcc gat ttg tat cct gat gtt gaa aat agt tta gca cca aca aca<br>Val Ser Asp Leu Tyr Pro Asp Val Glu Asn Ser Leu Ala Pro Thr Thr<br>675 680 685 | 2064 |
| gaa caa ttg gca gct gct ttc aaa gta tac aat gaa gat gaa aaa tta<br>Glu Gln Leu Ala Ala Ala Phe Lys Val Tyr Asn Glu Asp Glu Lys Leu<br>690 695 700 | 2112 |
| gca gac aaa aag tac aca caa tat aat atg gct agt gct tat gcg atg<br>Ala Asp Lys Lys Tyr Thr Gln Tyr Asn Met Ala Ser Ala Tyr Ala Met<br>705 710 715 720 | 2160 |
| ttg cta acc aat aag gat act gtt cct cgt gtc tat tat ggc gat tta<br>Leu Leu Thr Asn Lys Asp Thr Val Pro Arg Val Tyr Tyr Gly Asp Leu<br>725 730 735 | 2208 |
| tat aca gat gat ggt caa tat atg gca aca aag tca cca tac tat gat<br>Tyr Thr Asp Asp Gly Gln Tyr Met Ala Thr Lys Ser Pro Tyr Tyr Asp<br>740 745 750 | 2256 |
| gcg att aac act ttg cta aag gct aga gtt cag tat gtt gct ggt ggc<br>Ala Ile Asn Thr Leu Leu Lys Ala Arg Val Gln Tyr Val Ala Gly Gly<br>755 760 765 | 2304 |
| caa tcg atg tcc gtt gat agt aat gac gtg tta aca agt gtt cgc tat<br>Gln Ser Met Ser Val Asp Ser Asn Asp Val Leu Thr Ser Val Arg Tyr<br>770 775 780 | 2352 |
| ggt aaa gat gcc atg aca gct tct gac act gga aca tct gag acg cgt<br>Gly Lys Asp Ala Met Thr Ala Ser Asp Thr Gly Thr Ser Glu Thr Arg<br>785 790 795 800 | 2400 |
| act gaa ggt att gga gtc atc gtc agc aat aac gcg gag cta caa tta<br>Thr Glu Gly Ile Gly Val Ile Val Ser Asn Asn Ala Glu Leu Gln Leu<br>805 810 815 | 2448 |
| gag gat ggg cat act gtc aca ttg cat atg ggg gca gct cat aag aac<br>Glu Asp Gly His Thr Val Thr Leu His Met Gly Ala Ala His Lys Asn<br>820 825 830 | 2496 |
| caa gct tat cgt gct ttg tta tca aca act gca gat gga tta gct tat<br>Gln Ala Tyr Arg Ala Leu Leu Ser Thr Thr Ala Asp Gly Leu Ala Tyr<br>835 840 845 | 2544 |
| tat gat act gat gaa aat gca cct gtg gcg tac aca gat gct aac ggc<br>Tyr Asp Thr Asp Glu Asn Ala Pro Val Ala Tyr Thr Asp Ala Asn Gly<br>850 855 860 | 2592 |
| gat ttg att ttt acg aat gaa tca att tat ggt gta caa aat cca caa<br>Asp Leu Ile Phe Thr Asn Glu Ser Ile Tyr Gly Val Gln Asn Pro Gln<br>865 870 875 880 | 2640 |
| gtt tct ggt tac ttg gca gtt tgg gtt ccg gta ggt gcg caa caa gat<br>Val Ser Gly Tyr Leu Ala Val Trp Val Pro Val Gly Ala Gln Gln Asp<br>885 890 895 | 2688 |

-continued

| | | |
|---|---|---|
| caa gat gca cga acg gcc tct gat aca aca aca aac acg agt gat aaa<br>Gln Asp Ala Arg Thr Ala Ser Asp Thr Thr Thr Asn Thr Ser Asp Lys<br>            900                    905                   910 | | 2736 |
| gtg ttc cat tca aac gct gct ctt gat tct caa gtc atc tac gaa ggt<br>Val Phe His Ser Asn Ala Ala Leu Asp Ser Gln Val Ile Tyr Glu Gly<br>       915                   920                   925 | | 2784 |
| ttc tca aac ttc caa gca ttt gct aca gac agc agt gaa tat aca aac<br>Phe Ser Asn Phe Gln Ala Phe Ala Thr Asp Ser Ser Glu Tyr Thr Asn<br>      930                  935                 940 | | 2832 |
| gta gtc atc gct cag aat gcg gac caa ttt aag caa tgg ggt gtg aca<br>Val Val Ile Ala Gln Asn Ala Asp Gln Phe Lys Gln Trp Gly Val Thr<br>945                950                955               960 | | 2880 |
| agc ttc caa ttg gca cca caa tat cgt tca agt aca gat aca agt ttc<br>Ser Phe Gln Leu Ala Pro Gln Tyr Arg Ser Ser Thr Asp Thr Ser Phe<br>                  965               970              975 | | 2928 |
| ttg gat tca att att caa aac ggg tat gca ttc acg gat cgt tat gac<br>Leu Asp Ser Ile Ile Gln Asn Gly Tyr Ala Phe Thr Asp Arg Tyr Asp<br>              980                  985               990 | | 2976 |
| tta ggt tat ggc aca ccg aca aaa tat gga act gct gat cag ttg cgc<br>Leu Gly Tyr Gly Thr Pro Thr Lys Tyr Gly Thr Ala Asp Gln Leu Arg<br>       995                1000              1005 | | 3024 |
| gat gct att aaa gcc tta cat gct agc ggt att caa gcc att gcc<br>Asp Ala Ile Lys Ala Leu His Ala Ser Gly Ile Gln Ala Ile Ala<br>      1010              1015              1020 | | 3069 |
| gat tgg gtg ccg gac caa att tat aat ttg cca gag caa gaa tta<br>Asp Trp Val Pro Asp Gln Ile Tyr Asn Leu Pro Glu Gln Glu Leu<br>      1025              1030              1035 | | 3114 |
| gct act gtc aca aga aca aat tca ttt gga gat gac gat aca gat<br>Ala Thr Val Thr Arg Thr Asn Ser Phe Gly Asp Asp Asp Thr Asp<br>      1040              1045              1050 | | 3159 |
| tct gat att gac aat gcc tta tat gtt gta caa agt cgt ggg ggt<br>Ser Asp Ile Asp Asn Ala Leu Tyr Val Val Gln Ser Arg Gly Gly<br>      1055              1060              1065 | | 3204 |
| ggt caa tat caa gag atg tat ggt ggt gcc ttc tta gaa gag tta<br>Gly Gln Tyr Gln Glu Met Tyr Gly Gly Ala Phe Leu Glu Glu Leu<br>      1070              1075              1080 | | 3249 |
| cag gca ctc tat cca tcc cta ttt aaa gtg aat caa atc tca act<br>Gln Ala Leu Tyr Pro Ser Leu Phe Lys Val Asn Gln Ile Ser Thr<br>      1085              1090              1095 | | 3294 |
| ggc gtt cca att gat ggc agt gta aag att act gag tgg gcg gct<br>Gly Val Pro Ile Asp Gly Ser Val Lys Ile Thr Glu Trp Ala Ala<br>      1100              1105              1110 | | 3339 |
| aag tac ttc aat ggc tct aac atc caa ggt aaa ggt gct gga tac<br>Lys Tyr Phe Asn Gly Ser Asn Ile Gln Gly Lys Gly Ala Gly Tyr<br>      1115              1120              1125 | | 3384 |
| gta ttg aaa gat atg ggt tct aat aag tac ttt aag gtc gtt tcg<br>Val Leu Lys Asp Met Gly Ser Asn Lys Tyr Phe Lys Val Val Ser<br>      1130              1135              1140 | | 3429 |
| aac act gag gat ggt gac tac tta cca aaa cag tta act aat gat<br>Asn Thr Glu Asp Gly Asp Tyr Leu Pro Lys Gln Leu Thr Asn Asp<br>      1145              1150              1155 | | 3474 |
| ctg tca gaa act ggc ttt aca cac gat gat aaa gga atc atc tat<br>Leu Ser Glu Thr Gly Phe Thr His Asp Asp Lys Gly Ile Ile Tyr<br>      1160              1165              1170 | | 3519 |
| tat aca tta agt ggt tat cgt gcc caa aat gca ttt att caa gat<br>Tyr Thr Leu Ser Gly Tyr Arg Ala Gln Asn Ala Phe Ile Gln Asp<br>      1175              1180              1185 | | 3564 |
| gat gat aat aac tat tac tat ttt gat aaa aca ggt cat tta gta<br>Asp Asp Asn Asn Tyr Tyr Tyr Phe Asp Lys Thr Gly His Leu Val<br>      1190              1195              1200 | | 3609 |

```
aca ggt ttg caa aag att aat aac cat acc tac ttc ttc tta cct      3654
Thr Gly Leu Gln Lys Ile Asn Asn His Thr Tyr Phe Phe Leu Pro
    1205                1210                1215 aat ggt atc gaa ctg gtc aag agc ttc tta caa aac gaa gat ggt      3699
Asn Gly Ile Glu Leu Val Lys Ser Phe Leu Gln Asn Glu Asp Gly
    1220                1225                1230 aca att gtt tat ttc gat aag aaa ggt cat caa gtt ttt gat caa      3744
Thr Ile Val Tyr Phe Asp Lys Lys Gly His Gln Val Phe Asp Gln
    1235                1240                1245 tat ata act gat caa aat gga aat gcg tat tac ttt gat gat gct      3789
Tyr Ile Thr Asp Gln Asn Gly Asn Ala Tyr Tyr Phe Asp Asp Ala
    1250                1255                1260 ggt gta atg ctt aaa tca ggg ctt gca acg att gat gga cat caa      3834
Gly Val Met Leu Lys Ser Gly Leu Ala Thr Ile Asp Gly His Gln
    1265                1270                1275 cag tat ttt gat caa aat ggt gtg cag gtt aag gat aag ttt gtg      3879
Gln Tyr Phe Asp Gln Asn Gly Val Gln Val Lys Asp Lys Phe Val
    1280                1285                1290 att ggc act gat ggt tat aag tat tac ttt gaa cca ggt agt ggt      3924
Ile Gly Thr Asp Gly Tyr Lys Tyr Tyr Phe Glu Pro Gly Ser Gly
    1295                1300                1305 aac tta gct atc cta cgt tat gtg caa aat agt aag aat caa tgg      3969
Asn Leu Ala Ile Leu Arg Tyr Val Gln Asn Ser Lys Asn Gln Trp
    1310                1315                1320 ttc tat ttt gat ggt aat ggc cat gct gtc act ggt ttc caa aca      4014
Phe Tyr Phe Asp Gly Asn Gly His Ala Val Thr Gly Phe Gln Thr
    1325                1330                1335 att aat ggt aaa aaa caa tat ttc tat aat gat ggt cat caa agt      4059
Ile Asn Gly Lys Lys Gln Tyr Phe Tyr Asn Asp Gly His Gln Ser
    1340                1345                1350 aaa ggt gaa ttc att gat gca gac ggg gat act ttc tat acg agt      4104
Lys Gly Glu Phe Ile Asp Ala Asp Gly Asp Thr Phe Tyr Thr Ser
    1355                1360                1365 gcc act gat ggt cgc cta gta act ggt gtt cag aag att aat ggt      4149
Ala Thr Asp Gly Arg Leu Val Thr Gly Val Gln Lys Ile Asn Gly
    1370                1375                1380 att acc tat gct ttt gat aac aca gga aat ttg atc aca aat cag      4194
Ile Thr Tyr Ala Phe Asp Asn Thr Gly Asn Leu Ile Thr Asn Gln
    1385                1390                1395 tat tat caa tta gca gat ggt aaa tat atg ttg tta gat gat agt      4239
Tyr Tyr Gln Leu Ala Asp Gly Lys Tyr Met Leu Leu Asp Asp Ser
    1400                1405                1410 ggt cgt gcg aaa aca ggg ttt gta ttg caa gat ggt gta cta aga      4284
Gly Arg Ala Lys Thr Gly Phe Val Leu Gln Asp Gly Val Leu Arg
    1415                1420                1425 tac ttc gat caa aac ggt gag caa gtg aaa gat gct atc att gtg      4329
Tyr Phe Asp Gln Asn Gly Glu Gln Val Lys Asp Ala Ile Ile Val
    1430                1435                1440 gat cca gat act aac ttg agt tat tat ttc aat gca aca caa ggt      4374
Asp Pro Asp Thr Asn Leu Ser Tyr Tyr Phe Asn Ala Thr Gln Gly
    1445                1450                1455 gtc gct gta aaa aat gat tat ttc gag tat caa ggt aat tgg tat      4419
Val Ala Val Lys Asn Asp Tyr Phe Glu Tyr Gln Gly Asn Trp Tyr
    1460                1465                1470 tta aca gat gct aat tat caa ctt atc aaa ggt ttt aaa gca gtt      4464
Leu Thr Asp Ala Asn Tyr Gln Leu Ile Lys Gly Phe Lys Ala Val
    1475                1480                1485 gac gac agc tta caa cat ttt gat gaa gtc act ggt gta caa aca      4509
Asp Asp Ser Leu Gln His Phe Asp Glu Val Thr Gly Val Gln Thr
    1490                1495                1500
```

```
aaa gat agt gct tta ata agt gct cag ggt aag gtt tac caa ttt     4554
Lys Asp Ser Ala Leu Ile Ser Ala Gln Gly Lys Val Tyr Gln Phe
    1505                1510                1515 gat aat aat gga aat gct gtg tca gca taa                          4584
Asp Asn Asn Gly Asn Ala Val Ser Ala
1520                1525

<210> SEQ ID NO 2
<211> LENGTH: 1527
<212> TYPE: PRT
<213> ORGANISM: Leuconostoc mesenteroides

<400> SEQUENCE: 2

Met Pro Phe Thr Glu Lys Val Met Arg Lys Lys Leu Tyr Lys Val Gly
1               5                   10                  15

Lys Ser Trp Val Val Gly Gly Val Cys Ala Phe Ala Leu Thr Ala Ser
            20                  25                  30

Phe Ala Leu Ala Thr Pro Ser Val Leu Gly Asp Ser Ser Val Pro Asp
        35                  40                  45

Val Ser Ala Asn Asn Val Gln Ser Ala Ser Asp Asn Thr Thr Asp Thr
    50                  55                  60

Gln Gln Asn Thr Thr Val Thr Glu Glu Asn Asp Lys Val Gln Ser Ala
65                  70                  75                  80

Ala Thr Asn Asp Asn Val Thr Thr Ala Ala Ser Asp Thr Thr Gln Ser
                85                  90                  95

Ala Asp Asn Asn Val Thr Glu Lys Gln Ser Asp Asp His Ala Leu Asp
            100                 105                 110

Asn Glu Lys Val Asp Asn Lys Gln Asp Glu Val Ala Gln Thr Asn Val
        115                 120                 125

Thr Ser Lys Asn Glu Glu Ser Ala Val Ala Ser Thr Asp Thr Asp Pro
    130                 135                 140

Ala Glu Thr Thr Thr Asp Glu Thr Gln Gln Val Ser Gly Lys Tyr Val
145                 150                 155                 160

Glu Lys Asp Gly Ser Trp Tyr Tyr Phe Asp Asp Gly Lys Asn Ala
                165                 170                 175

Lys Gly Leu Ser Thr Ile Asp Asn Asn Ile Gln Tyr Phe Tyr Glu Ser
            180                 185                 190

Gly Lys Gln Ala Lys Gly Gln Tyr Val Thr Ile Asp Asn Gln Thr Tyr
        195                 200                 205

Tyr Phe Asp Lys Gly Ser Gly Asp Glu Leu Thr Gly Leu Gln Ser Ile
    210                 215                 220

Asp Gly Asn Ile Val Ala Phe Asn Asp Glu Gly Gln Gln Ile Phe Asn
225                 230                 235                 240

Gln Tyr Tyr Gln Ser Glu Asn Gly Thr Thr Tyr Tyr Phe Asp Asp Lys
                245                 250                 255

Gly His Ala Ala Thr Gly Ile Lys Asn Ile Glu Gly Lys Asn Tyr Tyr
            260                 265                 270

Phe Asp Asn Leu Gly Gln Leu Lys Lys Gly Phe Ser Gly Val Ile Asp
        275                 280                 285

Gly Gln Ile Met Thr Phe Asp Gln Glu Thr Gly Gln Glu Val Ser Asn
    290                 295                 300

Thr Thr Ser Glu Ile Lys Glu Gly Leu Thr Thr Gln Asn Thr Asp Tyr
305                 310                 315                 320

Ser Glu His Asn Ala Ala His Gly Thr Asp Ala Glu Asp Phe Glu Asn
                325                 330                 335

Ile Asp Gly Tyr Leu Thr Ala Ser Ser Trp Tyr Arg Pro Thr Gly Ile
```

```
                340                 345                 350
Leu Arg Asn Gly Thr Asp Trp Glu Pro Ser Thr Asp Thr Asp Phe Arg
            355                 360                 365
Pro Ile Leu Ser Val Trp Trp Pro Asp Lys Asn Thr Gln Val Asn Tyr
        370                 375                 380
Leu Asn Tyr Met Ala Asp Leu Gly Phe Ile Ser Asn Ala Asp Ser Phe
385                 390                 395                 400
Glu Thr Gly Asp Ser Gln Ser Leu Leu Asn Glu Ala Ser Asn Tyr Val
                405                 410                 415
Gln Lys Ser Ile Glu Met Lys Ile Ser Ala Gln Ser Thr Glu Trp
            420                 425                 430
Leu Lys Asp Ala Met Ala Ala Phe Ile Val Ala Gln Pro Gln Trp Asn
        435                 440                 445
Glu Thr Ser Glu Asp Met Ser Asn Asp His Leu Gln Asn Gly Ala Leu
        450                 455                 460
Thr Tyr Val Asn Ser Pro Leu Thr Pro Asp Ala Asn Ser Asn Phe Arg
465                 470                 475                 480
Leu Leu Asn Arg Thr Pro Thr Asn Gln Thr Gly Glu Gln Ala Tyr Asn
                485                 490                 495
Leu Asp Asn Ser Lys Gly Gly Phe Glu Leu Leu Ala Asn Gln Glu
            500                 505                 510
Asp Asn Ser Asn Val Val Val Glu Ala Glu Gln Leu Asn Trp Leu Tyr
        515                 520                 525
Tyr Leu Met Asn Phe Gly Thr Ile Thr Ala Asn Asp Ala Asp Ala Asn
        530                 535                 540
Phe Asp Gly Ile Arg Val Asp Ala Val Asp Asn Val Asp Ala Asp Leu
545                 550                 555                 560
Leu Gln Ile Ala Ala Asp Tyr Phe Lys Leu Ala Tyr Gly Val Asp Gln
                565                 570                 575
Asn Asp Ala Thr Ala Asn Gln His Leu Ser Ile Leu Glu Asp Trp Ser
            580                 585                 590
His Asn Asp Pro Leu Tyr Val Thr Asp Gln Gly Ser Asn Gln Leu Thr
        595                 600                 605
Met Asp Asp Tyr Val His Thr Gln Leu Ile Trp Ser Leu Thr Lys Ser
        610                 615                 620
Ser Asp Ile Arg Gly Thr Met Gln Arg Phe Val Asp Tyr Tyr Met Val
625                 630                 635                 640
Asp Arg Ser Asn Asp Ser Thr Glu Asn Glu Ala Ile Pro Asn Tyr Ser
                645                 650                 655
Phe Val Arg Ala His Asp Ser Glu Val Gln Thr Val Ile Ala Gln Ile
            660                 665                 670
Val Ser Asp Leu Tyr Pro Asp Val Glu Asn Ser Leu Ala Pro Thr Thr
        675                 680                 685
Glu Gln Leu Ala Ala Ala Phe Lys Val Tyr Asn Glu Asp Glu Lys Leu
        690                 695                 700
Ala Asp Lys Lys Tyr Thr Gln Tyr Asn Met Ala Ser Ala Tyr Ala Met
705                 710                 715                 720
Leu Leu Thr Asn Lys Asp Thr Val Pro Arg Val Tyr Tyr Gly Asp Leu
                725                 730                 735
Tyr Thr Asp Asp Gly Gln Tyr Met Ala Thr Lys Ser Pro Tyr Tyr Asp
            740                 745                 750
Ala Ile Asn Thr Leu Leu Lys Ala Arg Val Gln Tyr Val Ala Gly Gly
        755                 760                 765
```

```
Gln Ser Met Ser Val Asp Ser Asn Asp Val Leu Thr Ser Val Arg Tyr
            770                 775                 780

Gly Lys Asp Ala Met Thr Ala Ser Asp Thr Gly Thr Ser Glu Thr Arg
785                 790                 795                 800

Thr Glu Gly Ile Gly Val Ile Val Ser Asn Asn Ala Glu Leu Gln Leu
                    805                 810                 815

Glu Asp Gly His Thr Val Thr Leu His Met Gly Ala Ala His Lys Asn
                820                 825                 830

Gln Ala Tyr Arg Ala Leu Leu Ser Thr Thr Ala Asp Gly Leu Ala Tyr
            835                 840                 845

Tyr Asp Thr Asp Glu Asn Ala Pro Val Ala Tyr Thr Asp Ala Asn Gly
        850                 855                 860

Asp Leu Ile Phe Thr Asn Glu Ser Ile Tyr Gly Val Gln Asn Pro Gln
865                 870                 875                 880

Val Ser Gly Tyr Leu Ala Val Trp Val Pro Val Gly Ala Gln Gln Asp
                    885                 890                 895

Gln Asp Ala Arg Thr Ala Ser Asp Thr Thr Asn Thr Ser Asp Lys
            900                 905                 910

Val Phe His Ser Asn Ala Ala Leu Asp Ser Gln Val Ile Tyr Glu Gly
                915                 920                 925

Phe Ser Asn Phe Gln Ala Phe Ala Thr Asp Ser Ser Glu Tyr Thr Asn
930                 935                 940

Val Val Ile Ala Gln Asn Ala Asp Gln Phe Lys Gln Trp Gly Val Thr
945                 950                 955                 960

Ser Phe Gln Leu Ala Pro Gln Tyr Arg Ser Ser Thr Thr Ser Phe
                965                 970                 975

Leu Asp Ser Ile Ile Gln Asn Gly Tyr Ala Phe Thr Asp Arg Tyr Asp
                980                 985                 990

Leu Gly Tyr Gly Thr Pro Thr Lys Tyr Gly Thr Ala Asp Gln Leu Arg
                995                 1000                1005

Asp Ala Ile Lys Ala Leu His Ala Ser Gly Ile Gln Ala Ile Ala
    1010                1015                1020

Asp Trp Val Pro Asp Gln Ile Tyr Asn Leu Pro Glu Gln Glu Leu
    1025                1030                1035

Ala Thr Val Thr Arg Thr Asn Ser Phe Gly Asp Asp Thr Asp
    1040                1045                1050

Ser Asp Ile Asp Asn Ala Leu Tyr Val Val Gln Ser Arg Gly Gly
    1055                1060                1065

Gly Gln Tyr Gln Glu Met Tyr Gly Gly Ala Phe Leu Glu Glu Leu
    1070                1075                1080

Gln Ala Leu Tyr Pro Ser Leu Phe Lys Val Asn Gln Ile Ser Thr
    1085                1090                1095

Gly Val Pro Ile Asp Gly Ser Val Lys Ile Thr Glu Trp Ala Ala
    1100                1105                1110

Lys Tyr Phe Asn Gly Ser Asn Ile Gln Gly Lys Gly Ala Gly Tyr
    1115                1120                1125

Val Leu Lys Asp Met Gly Ser Asn Lys Tyr Phe Lys Val Val Ser
    1130                1135                1140

Asn Thr Glu Asp Gly Asp Tyr Leu Pro Lys Gln Leu Thr Asn Asp
    1145                1150                1155

Leu Ser Glu Thr Gly Phe Thr His Asp Asp Lys Gly Ile Ile Tyr
    1160                1165                1170

Tyr Thr Leu Ser Gly Tyr Arg Ala Gln Asn Ala Phe Ile Gln Asp
    1175                1180                1185
```

Asp Asp Asn Asn Tyr Tyr Tyr Phe Asp Lys Thr Gly His Leu Val
    1190                1195                1200

Thr Gly Leu Gln Lys Ile Asn Asn His Thr Tyr Phe Phe Leu Pro
    1205                1210                1215

Asn Gly Ile Glu Leu Val Lys Ser Phe Leu Gln Asn Glu Asp Gly
    1220                1225                1230

Thr Ile Val Tyr Phe Asp Lys Lys Gly His Gln Val Phe Asp Gln
    1235                1240                1245

Tyr Ile Thr Asp Gln Asn Gly Asn Ala Tyr Tyr Phe Asp Asp Ala
    1250                1255                1260

Gly Val Met Leu Lys Ser Gly Leu Ala Thr Ile Asp Gly His Gln
    1265                1270                1275

Gln Tyr Phe Asp Gln Asn Gly Val Gln Val Lys Asp Lys Phe Val
    1280                1285                1290

Ile Gly Thr Asp Gly Tyr Lys Tyr Tyr Phe Glu Pro Gly Ser Gly
    1295                1300                1305

Asn Leu Ala Ile Leu Arg Tyr Val Gln Asn Ser Lys Asn Gln Trp
    1310                1315                1320

Phe Tyr Phe Asp Gly Asn Gly His Ala Val Thr Gly Phe Gln Thr
    1325                1330                1335

Ile Asn Gly Lys Lys Gln Tyr Phe Tyr Asn Asp Gly His Gln Ser
    1340                1345                1350

Lys Gly Glu Phe Ile Asp Ala Asp Gly Asp Thr Phe Tyr Thr Ser
    1355                1360                1365

Ala Thr Asp Gly Arg Leu Val Thr Gly Val Gln Lys Ile Asn Gly
    1370                1375                1380

Ile Thr Tyr Ala Phe Asp Asn Thr Gly Asn Leu Ile Thr Asn Gln
    1385                1390                1395

Tyr Tyr Gln Leu Ala Asp Gly Lys Tyr Met Leu Leu Asp Asp Ser
    1400                1405                1410

Gly Arg Ala Lys Thr Gly Phe Val Leu Gln Asp Gly Val Leu Arg
    1415                1420                1425

Tyr Phe Asp Gln Asn Gly Glu Gln Val Lys Asp Ala Ile Ile Val
    1430                1435                1440

Asp Pro Asp Thr Asn Leu Ser Tyr Tyr Phe Asn Ala Thr Gln Gly
    1445                1450                1455

Val Ala Val Lys Asn Asp Tyr Phe Glu Tyr Gln Gly Asn Trp Tyr
    1460                1465                1470

Leu Thr Asp Ala Asn Tyr Gln Leu Ile Lys Gly Phe Lys Ala Val
    1475                1480                1485

Asp Asp Ser Leu Gln His Phe Asp Glu Val Thr Gly Val Gln Thr
    1490                1495                1500

Lys Asp Ser Ala Leu Ile Ser Ala Gln Gly Lys Val Tyr Gln Phe
    1505                1510                1515

Asp Asn Asn Gly Asn Ala Val Ser Ala
    1520                1525

<210> SEQ ID NO 3
<211> LENGTH: 4476
<212> TYPE: DNA
<213> ORGANISM: Leuconostoc mesenteroides
<220> FEATURE:
<221> NAME/KEY: CDS
<222> LOCATION: (1)..(4476)
<223> OTHER INFORMATION: mature CDS

<400> SEQUENCE: 3

```
aca cca agt gtt tta gga gac agt agt gta cct gat gtg agt gcg aat      48
Thr Pro Ser Val Leu Gly Asp Ser Ser Val Pro Asp Val Ser Ala Asn
1               5                   10                  15 aac gtt caa tct gct tca gat aat aca acg gat acg cag cag aac act      96
Asn Val Gln Ser Ala Ser Asp Asn Thr Thr Asp Thr Gln Gln Asn Thr
            20                  25                  30 acg gtt acc gaa gaa aat gat aaa gta cag tct gca gct act aat gac     144
Thr Val Thr Glu Glu Asn Asp Lys Val Gln Ser Ala Ala Thr Asn Asp
        35                  40                  45 aat gta aca aca gct gca agc gac aca aca caa tct gct gat aat aat     192
Asn Val Thr Thr Ala Ala Ser Asp Thr Thr Gln Ser Ala Asp Asn Asn
    50                  55                  60 gtg aca gaa aaa cag tca gat gat cat gca ctt gat aat gaa aaa gtc     240
Val Thr Glu Lys Gln Ser Asp Asp His Ala Leu Asp Asn Glu Lys Val
65                  70                  75                  80 gat aac aaa caa gat gaa gtc gct caa acc aat gtt act agc aaa aat     288
Asp Asn Lys Gln Asp Glu Val Ala Gln Thr Asn Val Thr Ser Lys Asn
                85                  90                  95 gag gaa tca gca gtt gct tca act gac act gat cct gct gaa acg aca     336
Glu Glu Ser Ala Val Ala Ser Thr Asp Thr Asp Pro Ala Glu Thr Thr
            100                 105                 110 act gac gaa aca caa caa gtt agc ggc aag tac gtt gaa aaa gac ggt     384
Thr Asp Glu Thr Gln Gln Val Ser Gly Lys Tyr Val Glu Lys Asp Gly
        115                 120                 125 agt tgg tat tat tat ttt gat gat ggc aaa aat gct aaa ggt tta tca     432
Ser Trp Tyr Tyr Tyr Phe Asp Asp Gly Lys Asn Ala Lys Gly Leu Ser
    130                 135                 140 acg ata gac aac aat att caa tat ttt tac gag agt ggt aaa caa gcc     480
Thr Ile Asp Asn Asn Ile Gln Tyr Phe Tyr Glu Ser Gly Lys Gln Ala
145                 150                 155                 160 aaa gga cag tat gtc aca att gat aat caa aca tat tat ttt gat aag     528
Lys Gly Gln Tyr Val Thr Ile Asp Asn Gln Thr Tyr Tyr Phe Asp Lys
                165                 170                 175 ggc tca ggt gat gag tta act ggt ctg caa agc att gat ggg aac ata     576
Gly Ser Gly Asp Glu Leu Thr Gly Leu Gln Ser Ile Asp Gly Asn Ile
            180                 185                 190 gtt gct ttt aac gat gaa ggg caa caa att ttt aat caa tat tac caa     624
Val Ala Phe Asn Asp Glu Gly Gln Gln Ile Phe Asn Gln Tyr Tyr Gln
        195                 200                 205 tct gaa aat ggt aca aca tac tac ttt gat gat aaa gga cac gct gct     672
Ser Glu Asn Gly Thr Thr Tyr Tyr Phe Asp Asp Lys Gly His Ala Ala
    210                 215                 220 acc ggt att aag aat atc gag ggc aaa aat tat tat ttt gat aat ctt     720
Thr Gly Ile Lys Asn Ile Glu Gly Lys Asn Tyr Tyr Phe Asp Asn Leu
225                 230                 235                 240 ggg caa cta aaa aaa ggc ttc tct ggt gtg att gat ggt caa ata atg     768
Gly Gln Leu Lys Lys Gly Phe Ser Gly Val Ile Asp Gly Gln Ile Met
                245                 250                 255 aca ttt gat cag gaa aca ggg caa gaa gtt tct aac aca act tct gaa     816
Thr Phe Asp Gln Glu Thr Gly Gln Glu Val Ser Asn Thr Thr Ser Glu
            260                 265                 270 ata aaa gaa ggt ttg acg act caa aac acg gat tat agc gaa cat aat     864
Ile Lys Glu Gly Leu Thr Thr Gln Asn Thr Asp Tyr Ser Glu His Asn
        275                 280                 285 gca gcc cac ggt acg gat gct gag gac ttt gaa aat att gac ggc tat     912
Ala Ala His Gly Thr Asp Ala Glu Asp Phe Glu Asn Ile Asp Gly Tyr
    290                 295                 300 tta aca gct agt tca tgg tat cgt cca aca ggt att tta cgt aac gga     960
Leu Thr Ala Ser Ser Trp Tyr Arg Pro Thr Gly Ile Leu Arg Asn Gly
```

```
                    305                 310                 315                 320
aca gac tgg gaa cct tct aca gat aca gat ttc aga cca ata ttg tca      1008
Thr Asp Trp Glu Pro Ser Thr Asp Thr Asp Phe Arg Pro Ile Leu Ser
                325                 330                 335 gtg tgg tgg cca gat aag aac acc cag gtc aat tat tta aat tac atg      1056
Val Trp Trp Pro Asp Lys Asn Thr Gln Val Asn Tyr Leu Asn Tyr Met
            340                 345                 350 gct gat tta ggg ttt atc agt aat gcg gac agt ttt gaa act ggg gat      1104
Ala Asp Leu Gly Phe Ile Ser Asn Ala Asp Ser Phe Glu Thr Gly Asp
        355                 360                 365 agc caa agc tta tta aat gaa gca agt aac tat gtt caa aaa tca att      1152
Ser Gln Ser Leu Leu Asn Glu Ala Ser Asn Tyr Val Gln Lys Ser Ile
    370                 375                 380 gaa atg aaa att agt gcg caa caa agt aca gag tgg tta aag gat gca      1200
Glu Met Lys Ile Ser Ala Gln Gln Ser Thr Glu Trp Leu Lys Asp Ala
385                 390                 395                 400 atg gcg gcc ttc att gtc gcg caa cca cag tgg aat gaa act agt gaa      1248
Met Ala Ala Phe Ile Val Ala Gln Pro Gln Trp Asn Glu Thr Ser Glu
                405                 410                 415 gat atg agc aat gac cat tta caa aat ggc gca tta act tat gtc aac      1296
Asp Met Ser Asn Asp His Leu Gln Asn Gly Ala Leu Thr Tyr Val Asn
            420                 425                 430 agt cca ctg aca cct gac gct aat tca aac ttt aga cta ctt aat cgg      1344
Ser Pro Leu Thr Pro Asp Ala Asn Ser Asn Phe Arg Leu Leu Asn Arg
        435                 440                 445 aca cca aca aac cag act ggt gaa caa gcg tat aat tta gat aat tca      1392
Thr Pro Thr Asn Gln Thr Gly Glu Gln Ala Tyr Asn Leu Asp Asn Ser
    450                 455                 460 aaa ggt ggt ttt gaa ttg ttg tta gcc aat cag gaa gat aat tca aac      1440
Lys Gly Gly Phe Glu Leu Leu Leu Ala Asn Gln Glu Asp Asn Ser Asn
465                 470                 475                 480 gtt gta gta gaa gca gaa caa ttg aat tgg tta tat tat tta atg aat      1488
Val Val Val Glu Ala Glu Gln Leu Asn Trp Leu Tyr Tyr Leu Met Asn
                485                 490                 495 ttt ggt acg att acg gcc aac gac gcg gat gct aat ttt gat ggt att      1536
Phe Gly Thr Ile Thr Ala Asn Asp Ala Asp Ala Asn Phe Asp Gly Ile
            500                 505                 510 cgt gta gat gca gtc gac aat gtg gat gct gat ttg tta caa att gct      1584
Arg Val Asp Ala Val Asp Asn Val Asp Ala Asp Leu Leu Gln Ile Ala
        515                 520                 525 gcc gat tat ttc aaa cta gct tac ggt gtt gat caa aat gat gct act      1632
Ala Asp Tyr Phe Lys Leu Ala Tyr Gly Val Asp Gln Asn Asp Ala Thr
    530                 535                 540 gct aat cag cat ctt tca att ttg gaa gat tgg agt cac aat gat cct      1680
Ala Asn Gln His Leu Ser Ile Leu Glu Asp Trp Ser His Asn Asp Pro
545                 550                 555                 560 ttg tat gta aca gat caa gga agc aat caa tta acc atg gat gat tat      1728
Leu Tyr Val Thr Asp Gln Gly Ser Asn Gln Leu Thr Met Asp Asp Tyr
                565                 570                 575 gtg cac aca caa tta atc tgg tct cta aca aaa tca tct gac ata cga      1776
Val His Thr Gln Leu Ile Trp Ser Leu Thr Lys Ser Ser Asp Ile Arg
            580                 585                 590 ggt aca atg cag cgc ttc gtg gat tat tat atg gtg gat cga tct aat      1824
Gly Thr Met Gln Arg Phe Val Asp Tyr Tyr Met Val Asp Arg Ser Asn
        595                 600                 605 gat agt aca gaa aac gaa gcc att cct aat tac agc ttt gta cgt gca      1872
Asp Ser Thr Glu Asn Glu Ala Ile Pro Asn Tyr Ser Phe Val Arg Ala
    610                 615                 620 cac gac agc gaa gtg caa acg gtt att gcc caa att gtt tcc gat ttg      1920
His Asp Ser Glu Val Gln Thr Val Ile Ala Gln Ile Val Ser Asp Leu
```

```
                 625                 630                 635                 640
tat cct gat gtt gaa aat agt tta gca cca aca aca gaa caa ttg gca              1968
Tyr Pro Asp Val Glu Asn Ser Leu Ala Pro Thr Thr Glu Gln Leu Ala
                     645                 650                 655 gct gct ttc aaa gta tac aat gaa gat gaa aaa tta gca gac aaa aag              2016
Ala Ala Phe Lys Val Tyr Asn Glu Asp Glu Lys Leu Ala Asp Lys Lys
                 660                 665                 670 tac aca caa tat aat atg gct agt gct tat gcg atg ttg cta acc aat              2064
Tyr Thr Gln Tyr Asn Met Ala Ser Ala Tyr Ala Met Leu Leu Thr Asn
             675                 680                 685 aag gat act gtt cct cgt gtc tat tat ggc gat tta tat aca gat gat              2112
Lys Asp Thr Val Pro Arg Val Tyr Tyr Gly Asp Leu Tyr Thr Asp Asp
         690                 695                 700 ggt caa tat atg gca aca aag tca cca tac tat gat gcg att aac act              2160
Gly Gln Tyr Met Ala Thr Lys Ser Pro Tyr Tyr Asp Ala Ile Asn Thr
705                 710                 715                 720 ttg cta aag gct aga gtt cag tat gtt gct ggt ggc caa tcg atg tcc              2208
Leu Leu Lys Ala Arg Val Gln Tyr Val Ala Gly Gly Gln Ser Met Ser
                     725                 730                 735 gtt gat agt aat gac gtg tta aca agt gtt cgc tat ggt aaa gat gcc              2256
Val Asp Ser Asn Asp Val Leu Thr Ser Val Arg Tyr Gly Lys Asp Ala
                 740                 745                 750 atg aca gct tct gac act gga aca tct gag acg cgt act gaa ggt att              2304
Met Thr Ala Ser Asp Thr Gly Thr Ser Glu Thr Arg Thr Glu Gly Ile
             755                 760                 765 gga gtc atc gtc agc aat aac gcg gag cta caa tta gag gat ggg cat              2352
Gly Val Ile Val Ser Asn Asn Ala Glu Leu Gln Leu Glu Asp Gly His
         770                 775                 780 act gtc aca ttg cat atg ggg gca gct cat aag aac caa gct tat cgt              2400
Thr Val Thr Leu His Met Gly Ala Ala His Lys Asn Gln Ala Tyr Arg
785                 790                 795                 800 gct ttg tta tca aca act gca gat gga tta gct tat tat gat act gat              2448
Ala Leu Leu Ser Thr Thr Ala Asp Gly Leu Ala Tyr Tyr Asp Thr Asp
                     805                 810                 815 gaa aat gca cct gtg gcg tac aca gat gct aac ggc gat ttg att ttt              2496
Glu Asn Ala Pro Val Ala Tyr Thr Asp Ala Asn Gly Asp Leu Ile Phe
                 820                 825                 830 acg aat gaa tca att tat ggt gta caa aat cca caa gtt tct ggt tac              2544
Thr Asn Glu Ser Ile Tyr Gly Val Gln Asn Pro Gln Val Ser Gly Tyr
             835                 840                 845 ttg gca gtt tgg gtt ccg gta ggt gcg caa caa gat caa gat gca cga              2592
Leu Ala Val Trp Val Pro Val Gly Ala Gln Gln Asp Gln Asp Ala Arg
         850                 855                 860 acg gcc tct gat aca aca aca aac acg agt gat aaa gtg ttc cat tca              2640
Thr Ala Ser Asp Thr Thr Thr Asn Thr Ser Asp Lys Val Phe His Ser
865                 870                 875                 880 aac gct gct ctt gat tct caa gtc atc tac gaa ggt ttc tca aac ttc              2688
Asn Ala Ala Leu Asp Ser Gln Val Ile Tyr Glu Gly Phe Ser Asn Phe
                     885                 890                 895 caa gca ttt gct aca gac agc agt gaa tat aca aac gta gtc atc gct              2736
Gln Ala Phe Ala Thr Asp Ser Ser Glu Tyr Thr Asn Val Val Ile Ala
                 900                 905                 910 cag aat gcg gac caa ttt aag caa tgg ggt gtg aca agc ttc caa ttg              2784
Gln Asn Ala Asp Gln Phe Lys Gln Trp Gly Val Thr Ser Phe Gln Leu
             915                 920                 925 gca cca caa tat cgt tca agt aca gat aca agt ttc ttg gat tca att              2832
Ala Pro Gln Tyr Arg Ser Ser Thr Asp Thr Ser Phe Leu Asp Ser Ile
         930                 935                 940 att caa aac ggg tat gca ttc acg gat cgt tat gac tta ggt tat ggc              2880
Ile Gln Asn Gly Tyr Ala Phe Thr Asp Arg Tyr Asp Leu Gly Tyr Gly
```

```
          945                 950                 955                 960
aca ccg aca aaa tat gga act gct gat cag ttg cgc gat gct att aaa         2928
Thr Pro Thr Lys Tyr Gly Thr Ala Asp Gln Leu Arg Asp Ala Ile Lys
                    965                 970                 975 gcc tta cat gct agc ggt att caa gcc att gcc gat tgg gtg ccg gac         2976
Ala Leu His Ala Ser Gly Ile Gln Ala Ile Ala Asp Trp Val Pro Asp
                    980                 985                 990 caa att tat aat ttg cca gag caa  gaa tta gct act gtc  aca aga aca       3024
Gln Ile Tyr Asn Leu Pro Glu Gln  Glu Leu Ala Thr Val  Thr Arg Thr
                    995                 1000                1005 aat tca  ttt gga gat gac gat  aca gat tct gat att  gac aat gcc          3069
Asn Ser  Phe Gly Asp Asp Asp  Thr Asp Ser Asp Ile  Asp Asn Ala
         1010                 1015                 1020 tta tat  gtt gta caa agt cgt  ggg ggt ggt caa tat  caa gag atg          3114
Leu Tyr  Val Val Gln Ser Arg  Gly Gly Gly Gln Tyr  Gln Glu Met
         1025                 1030                 1035 tat ggt  ggt gcc ttc tta gaa  gag tta cag gca ctc  tat cca tcc          3159
Tyr Gly  Gly Ala Phe Leu Glu  Glu Leu Gln Ala Leu  Tyr Pro Ser
         1040                 1045                 1050 cta ttt  aaa gtg aat caa atc  tca act ggc gtt cca  att gat ggc          3204
Leu Phe  Lys Val Asn Gln Ile  Ser Thr Gly Val Pro  Ile Asp Gly
         1055                 1060                 1065 agt gta  aag att act gag tgg  gcg gct aag tac ttc  aat ggc tct          3249
Ser Val  Lys Ile Thr Glu Trp  Ala Ala Lys Tyr Phe  Asn Gly Ser
         1070                 1075                 1080 aac atc  caa ggt aaa ggt gct  gga tac gta ttg aaa  gat atg ggt          3294
Asn Ile  Gln Gly Lys Gly Ala  Gly Tyr Val Leu Lys  Asp Met Gly
         1085                 1090                 1095 tct aat  aag tac ttt aag gtc  gtt tcg aac act gag  gat ggt gac          3339
Ser Asn  Lys Tyr Phe Lys Val  Val Ser Asn Thr Glu  Asp Gly Asp
         1100                 1105                 1110 tac tta  cca aaa cag tta act  aat gat ctg tca gaa  act ggc ttt          3384
Tyr Leu  Pro Lys Gln Leu Thr  Asn Asp Leu Ser Glu  Thr Gly Phe
         1115                 1120                 1125 aca cac  gat gat aaa gga atc  atc tat tat aca tta  agt ggt tat          3429
Thr His  Asp Asp Lys Gly Ile  Ile Tyr Tyr Thr Leu  Ser Gly Tyr
         1130                 1135                 1140 cgt gcc  caa aat gca ttt att  caa gat gat gat aat  aac tat tac          3474
Arg Ala  Gln Asn Ala Phe Ile  Gln Asp Asp Asp Asn  Asn Tyr Tyr
         1145                 1150                 1155 tat ttt  gat aaa aca ggt cat  tta gta aca ggt ttg  caa aag att          3519
Tyr Phe  Asp Lys Thr Gly His  Leu Val Thr Gly Leu  Gln Lys Ile
         1160                 1165                 1170 aat aac  cat acc tac ttc ttc  tta cct aat ggt atc  gaa ctg gtc          3564
Asn Asn  His Thr Tyr Phe Phe  Leu Pro Asn Gly Ile  Glu Leu Val
         1175                 1180                 1185 aag agc  ttc tta caa aac gaa  gat ggt aca att gtt  tat ttc gat          3609
Lys Ser  Phe Leu Gln Asn Glu  Asp Gly Thr Ile Val  Tyr Phe Asp
         1190                 1195                 1200 aag aaa  ggt cat caa gtt ttt  gat caa tat ata act  gat caa aat          3654
Lys Lys  Gly His Gln Val Phe  Asp Gln Tyr Ile Thr  Asp Gln Asn
         1205                 1210                 1215 gga aat  gcg tat tac ttt gat  gat gct ggt gta atg  ctt aaa tca          3699
Gly Asn  Ala Tyr Tyr Phe Asp  Asp Ala Gly Val Met  Leu Lys Ser
         1220                 1225                 1230 ggg ctt  gca acg att gat gga  cat caa cag tat ttt  gat caa aat          3744
Gly Leu  Ala Thr Ile Asp Gly  His Gln Gln Tyr Phe  Asp Gln Asn
         1235                 1240                 1245 ggt gtg  cag gtt aag gat aag  ttt gtg att ggc act  gat ggt tat          3789
Gly Val  Gln Val Lys Asp Lys  Phe Val Ile Gly Thr  Asp Gly Tyr
```

```
aag tat tac ttt gaa cca ggt agt ggt aac tta gct atc cta cgt      3834
Lys Tyr Tyr Phe Glu Pro Gly Ser Gly Asn Leu Ala Ile Leu Arg
    1265                1270                1275 tat gtg caa aat agt aag aat caa tgg ttc tat ttt gat ggt aat      3879
Tyr Val Gln Asn Ser Lys Asn Gln Trp Phe Tyr Phe Asp Gly Asn
1280                1285                1290 ggc cat gct gtc act ggt ttc caa aca att aat ggt aaa aaa caa      3924
Gly His Ala Val Thr Gly Phe Gln Thr Ile Asn Gly Lys Lys Gln
    1295                1300                1305 tat ttc tat aat gat ggt cat caa agt aaa ggt gaa ttc att gat      3969
Tyr Phe Tyr Asn Asp Gly His Gln Ser Lys Gly Glu Phe Ile Asp
1310                1315                1320 gca gac ggg gat act ttc tat acg agt gcc act gat ggt cgc cta      4014
Ala Asp Gly Asp Thr Phe Tyr Thr Ser Ala Thr Asp Gly Arg Leu
    1325                1330                1335 gta act ggt gtt cag aag att aat ggt att acc tat gct ttt gat      4059
Val Thr Gly Val Gln Lys Ile Asn Gly Ile Thr Tyr Ala Phe Asp
1340                1345                1350 aac aca gga aat ttg atc aca aat cag tat tat caa tta gca gat      4104
Asn Thr Gly Asn Leu Ile Thr Asn Gln Tyr Tyr Gln Leu Ala Asp
    1355                1360                1365 ggt aaa tat atg ttg tta gat gat agt ggt cgt gcg aaa aca ggg      4149
Gly Lys Tyr Met Leu Leu Asp Asp Ser Gly Arg Ala Lys Thr Gly
1370                1375                1380 ttt gta ttg caa gat ggt gta cta aga tac ttc gat caa aac ggt      4194
Phe Val Leu Gln Asp Gly Val Leu Arg Tyr Phe Asp Gln Asn Gly
    1385                1390                1395 gag caa gtg aaa gat gct atc att gtg gat cca gat act aac ttg      4239
Glu Gln Val Lys Asp Ala Ile Ile Val Asp Pro Asp Thr Asn Leu
1400                1405                1410 agt tat tat ttc aat gca aca caa ggt gtc gct gta aaa aat gat      4284
Ser Tyr Tyr Phe Asn Ala Thr Gln Gly Val Ala Val Lys Asn Asp
    1415                1420                1425 tat ttc gag tat caa ggt aat tgg tat tta aca gat gct aat tat      4329
Tyr Phe Glu Tyr Gln Gly Asn Trp Tyr Leu Thr Asp Ala Asn Tyr
1430                1435                1440 caa ctt atc aaa ggt ttt aaa gca gtt gac gac agc tta caa cat      4374
Gln Leu Ile Lys Gly Phe Lys Ala Val Asp Asp Ser Leu Gln His
    1445                1450                1455 ttt gat gaa gtc act ggt gta caa aca aaa gat agt gct tta ata      4419
Phe Asp Glu Val Thr Gly Val Gln Thr Lys Asp Ser Ala Leu Ile
1460                1465                1470 agt gct cag ggt aag gtt tac caa ttt gat aat aat gga aat gct      4464
Ser Ala Gln Gly Lys Val Tyr Gln Phe Asp Asn Asn Gly Asn Ala
    1475                1480                1485 gtg tca gca taa                                                   4476
Val Ser Ala
1490
```

<210> SEQ ID NO 4
<211> LENGTH: 1491
<212> TYPE: PRT
<213> ORGANISM: Leuconostoc mesenteroides

<400> SEQUENCE: 4

```
Thr Pro Ser Val Leu Gly Asp Ser Ser Val Pro Asp Val Ser Ala Asn
1               5                   10                  15

Asn Val Gln Ser Ala Ser Asp Asn Thr Thr Asp Thr Gln Gln Asn Thr
            20                  25                  30
```

```
Thr Val Thr Glu Glu Asn Asp Lys Val Gln Ser Ala Ala Thr Asn Asp
             35                  40                  45

Asn Val Thr Thr Ala Ala Ser Asp Thr Thr Gln Ser Ala Asp Asn Asn
 50                  55                  60

Val Thr Glu Lys Gln Ser Asp Asp His Ala Leu Asp Asn Glu Lys Val
 65                  70                  75                  80

Asp Asn Lys Gln Asp Glu Val Ala Gln Thr Asn Val Thr Ser Lys Asn
                 85                  90                  95

Glu Glu Ser Ala Val Ala Ser Thr Asp Thr Asp Pro Ala Glu Thr Thr
                100                 105                 110

Thr Asp Glu Thr Gln Gln Val Ser Gly Lys Tyr Val Glu Lys Asp Gly
            115                 120                 125

Ser Trp Tyr Tyr Tyr Phe Asp Asp Gly Lys Asn Ala Lys Gly Leu Ser
        130                 135                 140

Thr Ile Asp Asn Asn Ile Gln Tyr Phe Tyr Glu Ser Gly Lys Gln Ala
145                 150                 155                 160

Lys Gly Gln Tyr Val Thr Ile Asp Asn Gln Thr Tyr Tyr Phe Asp Lys
                165                 170                 175

Gly Ser Gly Asp Glu Leu Thr Gly Leu Gln Ser Ile Asp Gly Asn Ile
            180                 185                 190

Val Ala Phe Asn Asp Glu Gly Gln Gln Ile Phe Asn Gln Tyr Tyr Gln
        195                 200                 205

Ser Glu Asn Gly Thr Thr Tyr Tyr Phe Asp Lys Gly His Ala Ala
210                 215                 220

Thr Gly Ile Lys Asn Ile Glu Gly Lys Asn Tyr Tyr Phe Asp Asn Leu
225                 230                 235                 240

Gly Gln Leu Lys Lys Gly Phe Ser Gly Val Ile Asp Gly Gln Ile Met
                245                 250                 255

Thr Phe Asp Gln Glu Thr Gly Gln Glu Val Ser Asn Thr Thr Ser Glu
            260                 265                 270

Ile Lys Glu Gly Leu Thr Thr Gln Asn Thr Asp Tyr Ser Glu His Asn
        275                 280                 285

Ala Ala His Gly Thr Asp Ala Glu Asp Phe Glu Asn Ile Asp Gly Tyr
    290                 295                 300

Leu Thr Ala Ser Ser Trp Tyr Arg Pro Thr Gly Ile Leu Arg Asn Gly
305                 310                 315                 320

Thr Asp Trp Glu Pro Ser Thr Asp Thr Asp Phe Arg Pro Ile Leu Ser
                325                 330                 335

Val Trp Trp Pro Asp Lys Asn Thr Gln Val Asn Tyr Leu Asn Tyr Met
            340                 345                 350

Ala Asp Leu Gly Phe Ile Ser Asn Ala Asp Ser Phe Glu Thr Gly Asp
        355                 360                 365

Ser Gln Ser Leu Leu Asn Glu Ala Ser Asn Tyr Val Gln Lys Ser Ile
    370                 375                 380

Glu Met Lys Ile Ser Ala Gln Gln Ser Thr Glu Trp Leu Lys Asp Ala
385                 390                 395                 400

Met Ala Ala Phe Ile Val Ala Gln Pro Gln Trp Asn Glu Thr Ser Glu
                405                 410                 415

Asp Met Ser Asn Asp His Leu Gln Asn Gly Ala Leu Thr Tyr Val Asn
            420                 425                 430

Ser Pro Leu Thr Pro Asp Ala Asn Ser Asn Phe Arg Leu Leu Asn Arg
        435                 440                 445

Thr Pro Thr Asn Gln Thr Gly Glu Gln Ala Tyr Asn Leu Asp Asn Ser
    450                 455                 460
```

-continued

```
Lys Gly Gly Phe Glu Leu Leu Ala Asn Gln Glu Asp Asn Ser Asn
465                 470                 475                 480

Val Val Val Glu Ala Glu Gln Leu Asn Trp Leu Tyr Tyr Leu Met Asn
                485                 490                 495

Phe Gly Thr Ile Thr Ala Asn Asp Ala Asp Ala Asn Phe Asp Gly Ile
            500                 505                 510

Arg Val Asp Ala Val Asp Asn Val Asp Ala Asp Leu Leu Gln Ile Ala
        515                 520                 525

Ala Asp Tyr Phe Lys Leu Ala Tyr Gly Val Asp Gln Asn Asp Ala Thr
    530                 535                 540

Ala Asn Gln His Leu Ser Ile Leu Glu Asp Trp Ser His Asn Asp Pro
545                 550                 555                 560

Leu Tyr Val Thr Asp Gln Gly Ser Asn Gln Leu Thr Met Asp Asp Tyr
                565                 570                 575

Val His Thr Gln Leu Ile Trp Ser Leu Thr Lys Ser Ser Asp Ile Arg
            580                 585                 590

Gly Thr Met Gln Arg Phe Val Asp Tyr Tyr Met Val Asp Arg Ser Asn
        595                 600                 605

Asp Ser Thr Glu Asn Glu Ala Ile Pro Asn Tyr Ser Phe Val Arg Ala
    610                 615                 620

His Asp Ser Glu Val Gln Thr Val Ile Ala Gln Ile Val Ser Asp Leu
625                 630                 635                 640

Tyr Pro Asp Val Glu Asn Ser Leu Ala Pro Thr Thr Glu Gln Leu Ala
                645                 650                 655

Ala Ala Phe Lys Val Tyr Asn Glu Asp Glu Lys Leu Ala Asp Lys Lys
            660                 665                 670

Tyr Thr Gln Tyr Asn Met Ala Ser Ala Tyr Ala Met Leu Leu Thr Asn
        675                 680                 685

Lys Asp Thr Val Pro Arg Val Tyr Tyr Gly Asp Leu Tyr Thr Asp Asp
    690                 695                 700

Gly Gln Tyr Met Ala Thr Lys Ser Pro Tyr Tyr Asp Ala Ile Asn Thr
705                 710                 715                 720

Leu Leu Lys Ala Arg Val Gln Tyr Val Ala Gly Gly Gln Ser Met Ser
                725                 730                 735

Val Asp Ser Asn Asp Val Leu Thr Ser Val Arg Tyr Gly Lys Asp Ala
            740                 745                 750

Met Thr Ala Ser Asp Thr Gly Thr Ser Glu Thr Arg Thr Glu Gly Ile
        755                 760                 765

Gly Val Ile Val Ser Asn Asn Ala Glu Leu Gln Leu Glu Asp Gly His
    770                 775                 780

Thr Val Thr Leu His Met Gly Ala Ala His Lys Asn Gln Ala Tyr Arg
785                 790                 795                 800

Ala Leu Leu Ser Thr Thr Ala Asp Gly Leu Ala Tyr Tyr Asp Thr Asp
                805                 810                 815

Glu Asn Ala Pro Val Ala Tyr Thr Asp Ala Asn Gly Asp Leu Ile Phe
            820                 825                 830

Thr Asn Glu Ser Ile Tyr Gly Val Gln Asn Pro Gln Val Ser Gly Tyr
        835                 840                 845

Leu Ala Val Trp Val Pro Val Gly Ala Gln Gln Asp Gln Asp Ala Arg
    850                 855                 860

Thr Ala Ser Asp Thr Thr Thr Asn Thr Ser Asp Lys Val Phe His Ser
865                 870                 875                 880

Asn Ala Ala Leu Asp Ser Gln Val Ile Tyr Glu Gly Phe Ser Asn Phe
```

-continued

```
                885                 890                 895
Gln Ala Phe Ala Thr Asp Ser Ser Glu Tyr Thr Asn Val Val Ile Ala
            900                 905                 910
Gln Asn Ala Asp Gln Phe Lys Gln Trp Gly Val Thr Ser Phe Gln Leu
            915                 920                 925
Ala Pro Gln Tyr Arg Ser Ser Thr Asp Thr Ser Phe Leu Asp Ser Ile
            930                 935                 940
Ile Gln Asn Gly Tyr Ala Phe Thr Asp Arg Tyr Asp Leu Gly Tyr Gly
945                 950                 955                 960
Thr Pro Thr Lys Tyr Gly Thr Ala Asp Gln Leu Arg Asp Ala Ile Lys
            965                 970                 975
Ala Leu His Ala Ser Gly Ile Gln Ala Ile Ala Asp Trp Val Pro Asp
            980                 985                 990
Gln Ile Tyr Asn Leu Pro Glu Gln  Glu Leu Ala Thr Val  Thr Arg Thr
            995                 1000                1005
Asn Ser  Phe Gly Asp Asp  Thr Asp Ser Asp Ile  Asp Asn Ala
    1010                1015                1020
Leu Tyr  Val Val Gln Ser Arg  Gly Gly Gln Tyr  Gln Glu Met
    1025                1030                1035
Tyr Gly  Gly Ala Phe Leu Glu  Glu Leu Gln Ala Leu  Tyr Pro Ser
    1040                1045                1050
Leu Phe  Lys Val Asn Gln Ile  Ser Thr Gly Val Pro  Ile Asp Gly
    1055                1060                1065
Ser Val  Lys Ile Thr Glu Trp  Ala Ala Lys Tyr Phe  Asn Gly Ser
    1070                1075                1080
Asn Ile  Gln Gly Lys Gly Ala  Gly Tyr Val Leu Lys  Asp Met Gly
    1085                1090                1095
Ser Asn  Lys Tyr Phe Lys Val  Val Ser Asn Thr Glu  Asp Gly Asp
    1100                1105                1110
Tyr Leu  Pro Lys Gln Leu Thr  Asn Asp Leu Ser Glu  Thr Gly Phe
    1115                1120                1125
Thr His  Asp Asp Lys Gly Ile  Ile Tyr Tyr Thr Leu  Ser Gly Tyr
    1130                1135                1140
Arg Ala  Gln Asn Ala Phe Ile  Gln Asp Asp Asn  Asn Tyr Tyr
    1145                1150                1155
Tyr Phe  Asp Lys Thr Gly His  Leu Val Thr Gly Leu  Gln Lys Ile
    1160                1165                1170
Asn Asn  His Thr Tyr Phe Phe  Leu Pro Asn Gly Ile  Glu Leu Val
    1175                1180                1185
Lys Ser  Phe Leu Gln Asn Glu  Asp Gly Thr Ile Val  Tyr Phe Asp
    1190                1195                1200
Lys Lys  Gly His Gln Val Phe  Asp Gln Tyr Ile Thr  Asp Gln Asn
    1205                1210                1215
Gly Asn  Ala Tyr Tyr Phe Asp  Asp Ala Gly Val Met  Leu Lys Ser
    1220                1225                1230
Gly Leu  Ala Thr Ile Asp Gly  His Gln Gln Tyr Phe  Asp Gln Asn
    1235                1240                1245
Gly Val  Gln Val Lys Asp Lys  Phe Val Ile Gly Thr  Asp Gly Tyr
    1250                1255                1260
Lys Tyr  Tyr Phe Glu Pro Gly  Ser Gly Asn Leu Ala  Ile Leu Arg
    1265                1270                1275
Tyr Val  Gln Asn Ser Lys Asn  Gln Trp Phe Tyr Phe  Asp Gly Asn
    1280                1285                1290
```

```
Gly His Ala Val Thr Gly Phe Gln Thr Ile Asn Gly Lys Lys Gln
    1295                1300                1305

Tyr Phe Tyr Asn Asp Gly His Gln Ser Lys Gly Glu Phe Ile Asp
    1310                1315                1320

Ala Asp Gly Asp Thr Phe Tyr Thr Ser Ala Thr Asp Gly Arg Leu
    1325                1330                1335

Val Thr Gly Val Gln Lys Ile Asn Gly Ile Thr Tyr Ala Phe Asp
    1340                1345                1350

Asn Thr Gly Asn Leu Ile Thr Asn Gln Tyr Tyr Gln Leu Ala Asp
    1355                1360                1365

Gly Lys Tyr Met Leu Leu Asp Asp Ser Gly Arg Ala Lys Thr Gly
    1370                1375                1380

Phe Val Leu Gln Asp Gly Val Leu Arg Tyr Phe Asp Gln Asn Gly
    1385                1390                1395

Glu Gln Val Lys Asp Ala Ile Ile Val Asp Pro Asp Thr Asn Leu
    1400                1405                1410

Ser Tyr Tyr Phe Asn Ala Thr Gln Gly Val Ala Val Lys Asn Asp
    1415                1420                1425

Tyr Phe Glu Tyr Gln Gly Asn Trp Tyr Leu Thr Asp Ala Asn Tyr
    1430                1435                1440

Gln Leu Ile Lys Gly Phe Lys Ala Val Asp Asp Ser Leu Gln His
    1445                1450                1455

Phe Asp Glu Val Thr Gly Val Gln Thr Lys Asp Ser Ala Leu Ile
    1460                1465                1470

Ser Ala Gln Gly Lys Val Tyr Gln Phe Asp Asn Asn Gly Asn Ala
    1475                1480                1485

Val Ser Ala
    1490

<210> SEQ ID NO 5
<211> LENGTH: 27
<212> TYPE: DNA
<213> ORGANISM: Artificial Sequence
<220> FEATURE:
<223> OTHER INFORMATION: Forward primer

<400> SEQUENCE: 5
gcctcatttg ctcccgggac accaagt                                          27

<210> SEQ ID NO 6
<211> LENGTH: 27
<212> TYPE: DNA
<213> ORGANISM: Artificial Sequence
<220> FEATURE:
<223> OTHER INFORMATION: Reverse primer

<400> SEQUENCE: 6
tggtggttcg cgagttatgc tgacaca                                          27
```

US 8,053,635 B2

TRANSFORMED PLANT EXPRESSING A DEXTRANSUCRASE AND SYNTHESIZING A MODIFIED STARCH

CROSS-REFERENCE TO RELATED APPLICATIONS

This application is the national stage filing of PCT/EP2005/013954, filed Dec. 19, 2005, which claims priority to EP 040 29 934.9, filed Dec. 17, 2004, and U.S. Provisional Patent Application No. 60/637,900, filed Dec. 21, 2004, the disclosures of each of which is hereby incorporated by reference.

BACKGROUND OF THE INVENTION (i) Field of the Invention:

The present invention relates to plant cells and plants, which are genetically modified, wherein the genetic modification leads to the expression in plastids of such plant cells and plants of an enzyme having the activity of a dextransucrase. Furthermore, the present invention relates to means and methods for the manufacture of such plant cells and plants. Plant cells and plants of this type synthesise a modified starch. The present invention therefore also relates to the starch synthesised by the plant cells and plants according to the invention as well as to methods for the manufacture of the starch and to the manufacture of starch derivatives of this modified starch.

(ii) Description of the Related Art:

With respect to the increasing significance which has recently been ascribed to vegetal substances as regenerative sources of raw materials, one of the objects of biotechnological research is to try to adapt vegetal raw materials to the demands of the processing industry. In order to enable the use of regenerative raw materials in as many areas as possible, it is furthermore important to obtain a large variety of substances. Apart from oils, fats and proteins, polysaccharides constitute the essential regenerative raw materials derived from plants. Apart from cellulose, starch maintains an important position among the polysaccharides, being one of the most significant storage substances in higher plants.

Starch is deposited as granules in the chloroplasts of green leaves (transitory starch) and in amyloplasts of tubers, roots and seeds (storage starch) (Kossmann and Llyod 2000).

The polysaccharide starch is a polymer made up of chemically homogeneous basic components, namely the glucose molecules. However, it constitutes a highly complex mixture from various types of molecules which differ from each other in their degree of polymerization and in the degree of branching of the glucose chains. Therefore, starch is not a homogeneous raw material. One differentiates particularly between amylose-starch, a basically non-branched polymer made up of alpha-1,4-glycosidically branched glucose molecules, and amylopectin-starch which in turn is a complex mixture of various branched glucose chains. The branching results from additional alpha-1,6-glycosidic interlinkings.

In plant storage organs, starch biosynthesis takes place within the amyloplast and is the result of different reactions such as synthesis (polymerization of glucosyl residues), rearrangement and degradation, in which various starch synthases (E.C.2.4.1.21), transferases (branching (E.C.2.4.1.18) and disproportionating enzyme (E.C.2.4.1.25)), and hydrolytic enzymes (debranching enzyme (E.C.3.2.1.41)), respectively, play key roles.

In order to enable as wide a use of starch as possible, it seems to be desirable that plants be provided which are capable of synthesizing modified starch which is particularly suitable for various uses. One possibility to provide such plants—apart from breeding methods—is the specific genetic modification of the starch metabolism of starch-producing plants by means of recombinant DNA techniques.

Over the years, several studies have been done aimed at turning the amyloplast into a more versatile polysaccharide factory. For this purpose, several microbial enzymes have been equipped with a plastidial targeting transit, and their influence on starch structure and functionality has been investigated.

Certain bacteria possess an array of enzymes, so-called glucansucrases, which can attach (contiguous) 1,6-linked or 1,3-linked glucosyl residues to maltodextrins. With few exceptions, glucansucrases are extracellular enzymes, which are produced by lactic acid bacteria such as *Leuconostoc mesenteroides* strains, oral Streptococci, and some species of *Lactobacillus* and *Lactococcus* (Robyt 1995; van Geel-Schutten et al. 1999). In addition, they are produced by other bacteria such as some of the *Neisseria* strains (Hehre et al. 1949). These strains are involved in different processes in nature. Some of the strains colonize the oral cavity of humans and animals and can induce the formation of dental caries. Other strains can invade the throat such as the commensal *Neisseria* species. Some *Lactobacillus* species increase the viscosity of fermented milk (de Vuyst and Degeest 1999).

The glucansucrases catalyse the polymerisation of glucose residues from sucrose, which leads to the production of a large variety of α-glucans with different sizes and structures, and composed of diverse linkage types.

Glucansucrases can be classified according to the structure of the glucan formed, and in particular the nature and frequency of the glucosidic linkages synthesized.

Dextransucrase (DSR) (E.C.2.4.1.5) synthesizes a glucan, called dextran, mainly composed of α-(1→6) glucosyl residues in the main linear chain and branched by variable proportions of α-(1→2), α-(1→3) or α-(1→4) linkages (Jeanes et al., 1954; Sidebotham, 1975; Robyt, 1995).

Biosynthesis of dextrans is mediated by *Lactobacillus*, *Leuconostoc*, and *Streptococcus* bacteria in the presence of sucrose.

Nucleic acid sequences encoding dextransucrases are well known in the art and numerous different sequences have been identified for numerous different dextransucrases (GenBank Database).

Dextran produced by *Leuconostoc mesenteroides* NRRL B-512F is water-soluble, and consists of 95% α-(1→6) linkages in the main chain and 5% α-(1→3) side chains (van Cleve et al., 1956). Its biosynthesis is mediated by a dextransucrase DSR-S (EC 2.4.1.5), which is a 1,527 amino-acid glucosyltransferase (Wilke-Douglas et al., 1989; Monchois et al., 1997). Its catalytic properties can be summarized as follows: after cleavage of sucrose, the glucose residue can be transferred to a growing dextran chain by the so-called two-site insertion mechanism, or to acceptor molecules (Robyt, 1995; Monchois et al., 1999).

The sequence of the Dsr-S gene from *L. mesenteroides* NRRL B-512F has been reported in WO 89/12386 and by Quirasco et al (1999); GenBank (Accession AJ271107).

Most glucansucrases share a common structure composed of four different regions: a signal peptide, a variable region, a catalytic domain, and a glucan-binding domain (GBD). (Monchois et al., 1999, FEMS Microbiology Letters 177, 243-248; Monchois et al., 1999, FEMS Microbiology Reviews 23, 131-151).

The signal peptide consists of 35-38 amino acids and is responsible for secretion of the sucrases, when expressed by their natural bacterial hosts. The signal peptide is followed by a variable region of 140-261 amino acids. Janecek et al. (2000) showed that conserved, long repeat elements (A-like repeats) are present in the downstream part of this region of dextransucrases of *Leuconostoc mesenteroides* NRRL B-512F (DSR-S), NRRL B-1299 (DSR-B). It has been hypothesized that these repeats can play a role in glucan binding. Nevertheless, this region does not seem to be essential for enzyme activity because DSR-A, which is produced by *Leuconostoc mesenteroides* NRRL B-1299 and catalyses the formation of a polymer containing between 27 and 35% of α-(1→2) branched linkages in addition to α-(1→6) ones (Robyt et al, 1978), does not possess this region and is still active.

The catalytic domain is composed of about 900 amino acids and is highly conserved within the *Leuconostoc* and *Streptococcus* species (MacGregor et al. 1996). The catalytic domain is also called the sucrose-binding domain because it contains a catalytic triad of aspartic and glutamic acid residues that play an important role in binding and cleavage of sucrose molecules.

The glucan-binding domain is covering about 500 amino acids, and is composed of repeats named A, B, C, D that are defined by a consensus sequence (Monchois et al 1998, 1999). Nevertheless, the number and organization of these repeats is variable within glucansucrases, and it has been shown that the minimum number of these repeated units necessary to ensure glucan binding properties is different according to the enzymes, and more particularly is different for enzymes producing a soluble glucan than for those producing an insoluble one (Monchois et al., 1999)

The elongation of glucan chains by glucansucrases is quite different compared to that by starch synthases. First, the preferred substrate is sucrose instead of ADP-Glucose. Second, the glucose residues are added to the reducing end of a growing glucan chain by a so-called two-site insertion mechanism (Robyt 1995).

In addition, the branching of glucans does not take place by means of a branching enzyme as in starch biosynthesis, but by a so-called acceptor reaction catalyzed by the glucansucrases themselves (Robyt, 1995). The glucansucrase is thought to contain an acceptor-binding site that can bind acceptor molecules such as the nascent glucan chains or maltodextrins (Su and Robyt, 1994).

The efficiency to catalyse acceptor reactions, particularly with starch polymers or maltodextrins is nevertheless unpredictable, as the structure-function relationships underlying the acceptor reaction are not understood and is poorly documented. It seems nevertheless that the relative acceptor efficiency depends on the size of the acceptor molecules (Fu et al. 1990), and it is uncertain that amylopectine and amylose may be acceptor molecules for glucansucrases.

Starch polymer modification has been achieved by targeting the *Escherichia coli* glycogen synthase (GLGA) and the glycogen branching enzyme (GLGB) to the potato amyloplast (Shewmaker et al. 1994; Kortstee et al. 1996). In both cases, the natural balance of chain elongation and branching was disturbed, resulting in starch granules with altered physical properties, and with more heavily branched polymers.

Attachment of novel glycosyl residues to starch polymers has also been an objective. For this purpose, a *Bacillus subtilis* levansucrase (E.C.2.4.1.10) was introduced in potato tuber amyloplasts (Gerrits et al. 2001). Levansucrase can polymerize the fructose moiety of the donor substrate sucrose into a high molecular weight fructan. Nevertheless, the starch yield was severely compromised and the starch morphology was dramatically altered.

It has also been tried to convert starch in planta into high-value cyclic oligosaccharides, which can accommodate hydrophobic substances in their apolar cavity and can be used in various food and pharmaceutical applications. A cyclodextrin glycosyltransferase (CGTase; E.C.2.4.1.19) from *Klebsiella pneumoniae* was introduced into potato amyloplasts (Oakes et al. 1991) for cyclodextrin production. Only 0.01% of the endogenous starch was converted to the desired product, and this product was difficult to recover from the plant material.

These examples demonstrate that bacterial enzymes can be potentially powerful tools for starch modification, but that their performance in the plant are unpredictable beforehand (Kok-Jacob A. et al, 2003).

SUMMARY OF THE INVENTION

The object of the present invention is therefore based on providing modified starch, new plant cells and/or plants, which synthesise such a modified starch, as well as methods for producing said plants.

DETAILED DESCRIPTION OF THE INVENTION

Figure 1:
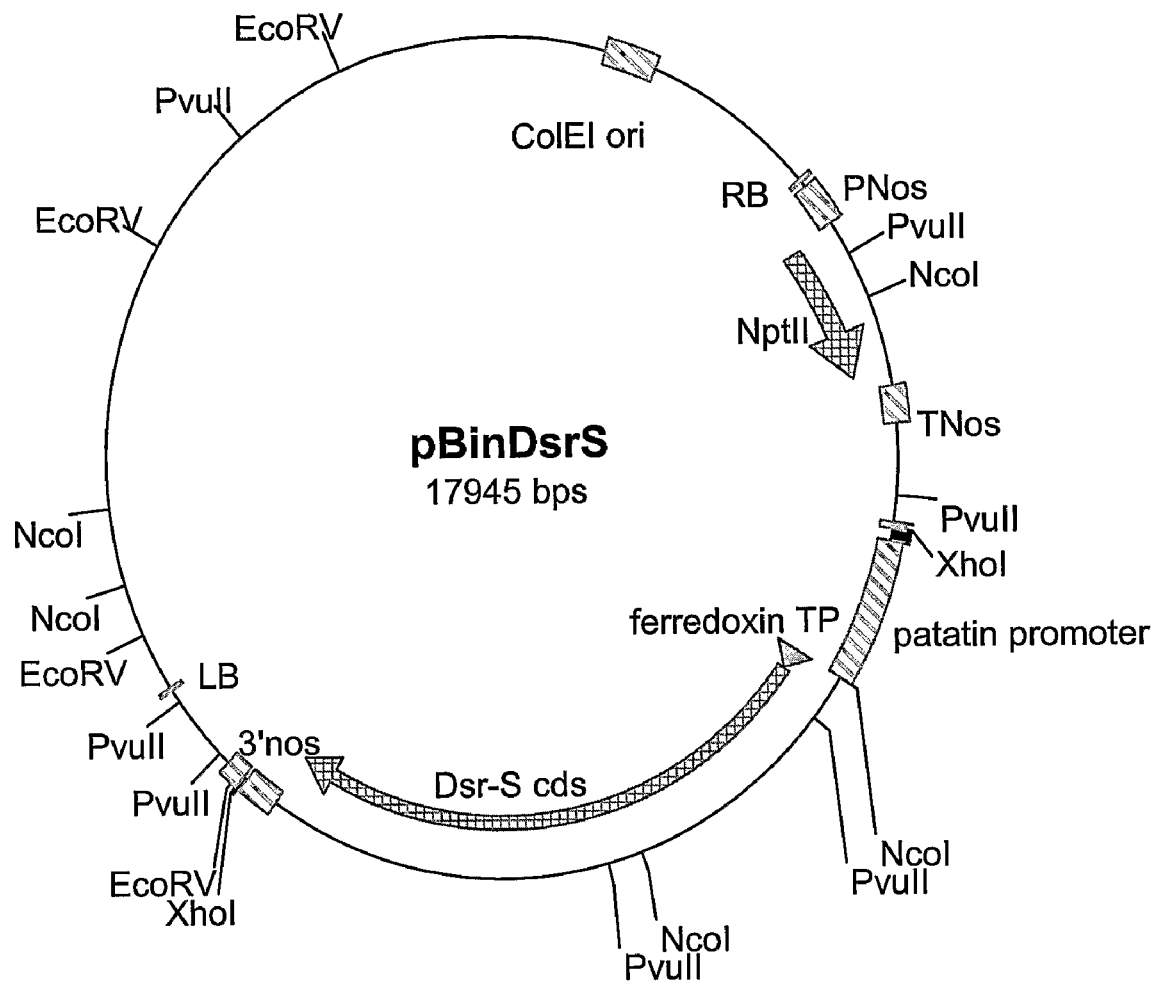
FIG. 1: map of plasmid pBinDsrS

Therefore, the present invention relates to genetically modified plant cells or genetically modified plants characterized in that they show an enzymatic activity of a dextransucrase DSR-S protein in plastids and wherein said genetically modified plant cells or genetically modified plants synthesize a modified starch in comparison to starch synthesized by corresponding non-genetically modified wild-type plant cells or wild type plants, respectively.

The term "genetically modified" or "transformed" refers to a plant cell or a plant having stably integrated in its genome at least one transgene. Preferentially, the transgene comprises a chimeric nucleic acid sequence comprising at least one element originating from an other organism than the transformed plant cell or transformed plant (heterologous transgene). Particularly, the transgene is a recombinant transgene which comprises at least a promoter, a coding sequence and optionally a termination signal. More preferably the coding sequence of the recombinant transgene encodes a dextransucrase protein, most preferably a dextransucrase DSR-S protein.

In conjunction with the present invention, the term "wild type plant cell" or "wild type plant" means that the plant cells or plants concerned were used as starting material for the manufacture of the plant cells according to the invention, i.e. their genetic information, apart from the introduced genetic modification, corresponds to that of a plant cell according to the invention.

In conjunction with the present invention, the term "corresponding" means that, in the comparison of several objects, the objects concerned that are compared with one another have been kept under the same conditions. In conjunction with the present invention, the term "corresponding" in conjunction with "wild type plant cell" or "wild type plant" means that the plant cells or plants, which are compared with one another, have been raised under the same cultivation conditions and that they have the same cultivation age.

Here, within the framework of the present invention, the term "activity" means the expression of a transgene coding sequence and/or the presence of the protein encoded by a transgene coding sequence and/or the presence of the product produced by the protein encoded by the transgene in the genetically modified plant cells or genetically modified plants, respectively.

The expression of a coding sequence of a transgene can, for example, be determined by measuring the quantity of transcripts of the transgene, e.g. using Northern blot analysis or RT-PCR.

The presence of a protein encoded by a transgene, which results in an activity of the respective protein in the genetically modified plant cells or genetically modified plants concerned, can, for example, be determined by immunological methods such as Western blot analysis, ELISA (Enzyme Linked Immuno Sorbent Assay) or RIA (Radio Immune Assay). In case the transgene encodes a dextransucrase DSR-S protein the presence of the DSR-S protein in genetically modified plant cells or genetically modified plants can be demonstrated, for example, with the help of native acrylamide gel electrophoresis. In doing so, plant cell or plant extracts containing proteins are first separated electrophoretically and, after incubation of the acrylamide gels in respective buffers containing sucrose, the acrylamide gels will be stained with the periodic acid-Shiff stain (Miller and Robyt, 1986, Analytical Biochemistry 156, 357-363; WO 00 47727).

The presence of the product dextran produced in plant cells according to the invention or plants according to the invention having been transformed with a nucleic acid sequence encoding a dextransucrase DSR-S protein can be demonstrated e.g. by immunological analysis according to the method described in example 3 of the present specification.

In conjunction with the present invention, the term "dextransucrase DSR-S protein" is to be understood as an enzyme catalysing the synthesis of dextran from sucrose. The dextran synthesized is composed of alpha-1,6-linked glucose units in the main chain and reveals alpha 1,3-linked side chains. Preferrably the dextransucrase protein of the invention synthesizes a dextran having around 5% alpha-1,3-linkages.

The term "dextransucrase DSR-S protein" is further defined as an enzyme having an identity of at least 70%, preferably at least 80%, more preferably at least 90%, and still more preferably at least 95% with the amino acid sequence identified under SEQ ID N0: 2 or SEQ ID N0: 4, and having the same catalytic properties than the enzyme encoded by the Dsr-S gene (accession AJ271107) from *L. mesenteroides*.

In conjunction with the present invention, the term "transgene" is understood to mean such a molecule that either does not occur naturally in the corresponding non-genetically modified wild type plant cells or non-genetically modified wildtype plants, or that does not occur naturally in the concrete spatial arrangement in non-genetically modified wild type plant cells or non-genetically modified wildtype plants, or that is localised at a place in the genome of the non-genetically modified wild type plant cell or non-genetically modified wildtype plant at which it does not occur naturally.

In conjunction with the invention the term "recombinant" means a nucleic acid molecule which consists of different elements, the combination or specific spatial arrangement of which does not occur naturally in plant cells or plants.

A large number of techniques are available for the introduction of DNA into a plant host cell. These techniques include the transformation of plant cells with T-DNA using *Agrobacterium tumefaciens* or *Agrobacterium rhizogenes* as the transformation medium, the fusion of protoplasts, injection, the electroporation of DNA, the introduction of DNA by means of the biolistic approach as well as other possibilities.

The use of *agrobacteria*-mediated transformation of plant cells has been intensively investigated and adequately described in EP 120516; Hoekema, I N: The Binary Plant Vector System Offsetdrukkerij Kanters B. V., Alblasserdam (1985), Chapter V; Fraley et al., Crit. Rev. Plant Sci. 4, 1-46 and by An et al. EMBO J. 4, (1985), 277-287. For the transformation of potato, see Rocha-Sosa et al., EMBO J. 8, (1989), 29-33, for example.

The transformation of monocotyledonous plants by means of vectors based on *agrobacterium* transformation has also been described (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Bio/Technology 13, (1995), 486-492; Conner and Domisse, Int. J. Plant Sci. 153 (1992), 550-555; Ritchie et al, Transgenic Res. 2, (1993), 252-265). An alternative system to the transformation of monocotyledonous plants is transformation by means of the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), protoplast transformation, electroporation of partially permeabilised cells and the introduction of DNA by means of glass fibres. In particular, the transformation of maize has been described in the literature many times (cf. e.g. WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726).

The successful transformation of other types of cereal has also already been described, for example for barley (Wan and Lemaux, see above; Ritala et al., see above; Krens et al., Nature 296, (1982), 72-74) and for wheat (Nehra et al., Plant J. 5, (1994), 285-297). All the above methods are suitable within the framework of the present invention.

In conjunction with the present invention, the introduced nucleic acid may be integrated into the nuclear genome or into the plastidial genome of the plant cell.

The classical way of transfecting plastids involves bombarding leaves with microprojectiles carrying DNA molecules (Svab et al., 1993). Today, stable plastid transfection is routinely performed in the tobacco species *N. tabaccum* (Svab and Maliga, 1990; Svab et al., 1993). There has been recent progress in rice (Khan and Maliga, 1999), *Arabidopsis thaliana* (Sikdar et al., 1998), potato (Sidorov et al, 1999), colza (WO 00/39313), tomato (Ruf et al., 2001) and soybean (WO 04/053133). Examples of methods for obtaining transplastomic plants have been described in Patent Application WO 04/055191.

Amongst other things, the plant cells according to the invention and the plants according to the invention can be differentiated from wild type plant cells and wild type plants respectively in that they contain at least one copy of the foreign nucleic acid molecule stably integrated within their genome, wherein the foreign nucleic acid molecule encodes a dextransucrase DSR-S protein.

Furthermore, the plant cells according to the invention and the plants according to the invention can preferably be differentiated from wild type plant cells or wild type plants respectively by the following characteristic: the plant cells according to the invention or plants according to the invention have transcripts of the introduced nucleic acid molecules. These can be verified, for example, by Northern blot analysis or by RT-PCR (Reverse Transcription Polymerase Chain Reaction). Preferably, the plant cells according to the invention and the plants according to the invention contain a protein, which is coded by an introduced nucleic acid molecule. This can be demonstrated by immunological methods, for example, in particular by a Western Blot Analysis.

Furthermore the plant cells according to the invention and the plants according to the invention can more preferably be differentiated from wild type plant cells or wild type plants, respectively, by the characteristics that they synthesize dextran. Preferably the plant cells of the invention or the plants of the invention produce dextran in their plastids.

The terms "starch which is modified in comparison to starch synthesized by wild-type plant cells or "modified starch" mean a starch which, when compared to starch synthesized in wild-type plants, differs for example in its physico-chemical properties, the pastification behavior, the size and/or the shape of the starch granule.

Compared with wild-type starch, such starch may be modified in particular with respect to its viscosity and/or the gel formation properties of the glues of this starch and/or its capability to be digested.

The modification in respect to the viscosity can be measured by several means, and in particular by means of a Thermo Haake rheoscope (Thermo Electron Cooperation) according to the manufacturer's instructions or by means of a Rapid Visco Analyser (RVA), as for example the Rapid Visco Analyser Super3 (Newport Scientific Pty Ltd, Investment Support Group, Warriewod NSW 2102, Australia). The viscosity values are indicated in Centipoise (cP) in accordance with the manufacturer's operating manuals, which are incorporated into the description herewith by reference.

A preferred way to determine the viscosity characteristics by means of a Rapid Visco Analyser (RVA) and the parameters which are used for the comparison of different samples are described in the general methods (method 1) of the present invention.

An other preferred way to determine the viscometric profiles by means of a thermo Haake rheoscope is described in the general methods (method 2) of the present invention.

The determination of the gel formation properties of the glues of the starch (or gel strength) can be determined by means of a Texture Analyser, as for example the Texture Analyser TA-XT2 (Stable Micro Systems—Surrey, UK) in accordance with the manufacturer's operating manual, which is incorporated into the description herewith by reference.

A preferred way to determine the gel formation properties of the glues of the starch by means of the Texture Analyser TA-XT2 is described in the general methods (method 3) of the present invention.

The capability to be digested can be determined by the determination of the percentage of digested starch, using the methodology of Englyst H. N. et al., European Journal of Clinical Nutrition 4, Suppl. 2, S33-S50, which is incorporated into the description herewith by reference, based on the determination of resistant starches RS Type II, which is the indigestible retrograded starch that is obtained, for example, by thermal and/or enzymatic treatment and then retrograded.

The method of Englyst can be modified in correspondence with the information on the determination of RS content in WO 00/02926, incorporated into the description herewith by reference. The resulting method is described in the general methods (method 4) of the present invention.

Further, the present invention relates to genetically modified plant cells or genetically modified plants of the invention characterized in that said plant cells or said plants, respectively, synthesize a modified starch which has a decreased end viscosity and/or an increased digestibility, in comparison to starch synthesized by wild-type plant cells.

In conjunction with the invention, the end viscosity can be measured by means of a rheoscope, particularly a Thermo Haake rheoscope or a Rapid Visco Analyser. Preferred methods for determination of the end viscosity are described in general methods (methods 1 and 2) of the present invention.

Preferably, the decrease of the end viscosity measured by means of a rheoscope, particularly a Thermo Haake rheoscope, is at least of 15%, preferred at least of 20%, more preferred at least of 25%, most preferred at least of 30%.

In conjunction with the invention, the digestibility can be measured according to the method of Englyst, or by the method of Englyst modified according to WO 00/02926. A preferred method for the determination of the digestibility is described in general methods (method 4) of the present invention.

Preferably, the increase in digestibility measured according to the method of Englyst or to the method of Englyst modified in correspondence with the information on the determination of RS content in WO 00/02926, is at least of 12%, preferred at least of 13%; more preferred at least of 14%, most preferred at least of 15%.

Furthermore, the invention relates to genetically modified plant cells according to the invention or genetically modified plants according to the invention, having integrated into its genome a transgene comprising linked to one another in a functional fashion in the direction of the transcription a promoter sequence which initiates transcription in plant cells, a heterologous nucleic acid sequence encoding a dextransucrase DSR-S protein, and optionally a termination sequence which is active in plant cells.

In conjunction with the present invention, the term "genome" is to be understood to mean the totality of the genetic material present in a plant cell. It is known to the person skilled in the art that, as well as the cell nucleus, other compartments (e.g. plastids, mitochondrions) also contain genetic material.

In a preferred embodiment, the nucleic acid construct is integrated into the nuclear genome of the plant cell. Transport of the dextransucrase protein into a particular cellular compartment, such as plastid, may therefore be accomplished by the use of a transit peptide to target the cellular compartment of interest. The nucleic acid sequence encoding the transit peptide is inserted in front of the coding sequence. Sequences encoding a transit peptide may be derived from any nucleic acid sequence encoding a plant protein which is expressed in the cytoplasm and translocated to the cellular compartment of interest. The transit peptide can be identified by comparing the messenger RNA encoding the particular polypeptide with the amino acid sequence of the mature protein. The amino acid sequences absent from the mature protein and coded for by the corresponding messenger RNA beginning at the initiation codon, usually a methionine, will normally be the transit peptide, or will normally contain the transit peptide. The skilled person will be able to determine sequences encoding transit peptides using a program for prediction of transit peptide, as for example Chloro 1.1 Server (Emanuelsson O. et al., 1999, Protein Science: 8:978-984)

The transit peptide is the amino acid sequence capable of directing a protein joined to the transit peptide to a cellular compartment of interest and may be the whole naturally occurring (wild-type) transit peptide, a functional fragment thereof, a functional mutant thereof, or a chimeric transit peptide wherein at least two transit peptides are associated to each other or of parts of different transit peptides associated to each other in a functional manner. Such a chimeric transit peptide is reported as an optimised transit peptide in EP0508909 and EP0924299.

The nucleic acid encoding a transit peptide may be heterologous in respect to the nucleic acid sequence encoding the enzyme fused to it, meaning that the nucleic acid sequence encoding the transit peptide and the nucleic acid sequence encoding the enzyme to be directed to the plastids originate from different genes which again can originate from different species.

A transit peptide dedicated to target the enzyme translationally joined to it to a plastid, such as chloroplast or amyloplast, is called a plastidial transit peptide.

The present invention further relates to genetically modified plant cells of the invention or genetically modified plants of the invention having integrated into its genome a nucleic acid construct comprising linked to one another in a functional fashion in the direction of the transcription a promoter sequence which initiates transcription in plant cells, a heterologous nucleic acid sequence encoding a plastidial transit peptide translationally fused with a heterologous nucleic acid sequence encoding a dextransucrase DSR-S protein, and optionally a termination sequence which is active in plant cells.

The term "linked to one another in a functional fashion" means that the elements of the nucleic acid construct are linked to one another in such a way which permits the expression of the coding region.

In conjunction with the invention the term "translationally fused" shall mean a fusion of nucleic acid sequences in such a way that they represent a single open reading frame, which upon transcription leads to the production of a single messenger RNA encoding a single protein, when translated.

Plastidial transit peptides may be selected from the group comprising the transit peptide of a gene encoding a waxy protein (Klösgen et al, Mol Gen Genet. 217 (1989), 155-161), the ribulose bisphosphate carboxylase small subunit (Wolter et al, Proc. Natl. Acad. Sci. USA 85 (1988), 846-850; Nawrath et al., Proc. Natl. Acad. Sci. 10 USA 91 (1994), 12760-12764), NADP-malate dehydrogenase (Gallardo et al., Planta 197 (1995), 324-332), Gluthation-reductase (Creissen et al., Plant J. 8 (1995), 167-175), EPSPS (U.S. Pat. No. 5,188,642), and an optimised transit peptide described in EP0508909 and EP0924299. These examples are not limiting.

In a preferred embodiment, a nucleic acid encoding a plastidial transit peptide of the ferredoxin reductase gene is translationally fused with the nucleic acid sequence encoding a dextransucrase DSR-S protein (Smeekens et al, 1985; Pilon et al, 1995).

In a further preferred embodiment, the plastidial transit sequence of the ferredoxin reductase gene originates from spinach.

In an other preferred embodiment, a nucleic acid sequence encoding the optimised plastidial transit peptide described in EP0508909 and EP0924299 is translationally fused with the nucleic acid sequence encoding a dextransucrase DSR-S protein.

The technologies used for the construction of the nucleic acid construct of the invention are well known to the skilled person. As non-limiting examples, it is possible to mention the technologies described in Sambrook et al. (1989, Molecular Cloning: *A Laboratory Manual*, Nolan C. ed., New York: Cold Spring Harbor Laboratory Press).

Furthermore, plant and/or progeny thereof, which contain a plant cell according to the invention, are also the subject matter of the invention. Plants of this type can be produced from the plant cell according to the invention by regeneration, using methods known to the person skilled in the art, as for example methods described in "plant Cell Culture Protocols" 1999, edited by R. D. Hall, Humana Press, ISBN 0-89603-549-2.

In principle, the plants according to the invention can be plants of any plant species, i.e. both monocotyledonous and dicotyledonous plants. Preferably they are useful plants, i.e. plants, which are cultivated by people for the purposes of food or for technical, in particular industrial purposes.

In a further preferred embodiment, the plant according to the invention is a starch-storing plant. The term "starch-storing plants" includes all plants with starch-storing plant parts such as, for example, maize, rice, wheat, rye, oat, barley, cassaya, potato, sago, mung bean, pea or sorghum. Preferred starch-storing plant parts are, for example, tubers, storage roots and grains containing an endosperm; tubers are particularly preferred; tubers of potato plants are especially preferred.

In a further preferred embodiment, the present invention relates to a starch-storing plant according to the invention which is a potato plant.

In conjunction with the present invention, the term "potato plant" or "potato" means plant species of the genus *Solanum*, in particular tuber-producing species of the genus *Solanum* and especially *Solanum tuberosum*.

The present invention also relates to propagation material of plants according to the invention containing a plant cell according to the invention.

Here, the term "propagation material" includes those constituents of the plant that are suitable for producing offspring by vegetative or sexual means. Cuttings, callus cultures, rhizomes or tubers, for example, are suitable for vegetative propagation. Other propagation material includes, for example, fruits, seeds, seedlings, protoplasts, cell cultures, etc. Preferably, the propagation material is seeds and particularly preferably tubers.

In a further embodiment, the present invention relates to harvestable plant parts of plants according to the invention such as fruits, storage roots, blooms, buds, shoots or stems, preferably seeds or tubers, wherein these harvestable parts contain plant cells according to the invention.

The present invention also relates to a method for the manufacture of genetically modified plants according to the invention wherein a) a plant cell is transformed with a nucleic acid molecule comprising a nucleic acid molecule encoding a dextransucrase DSR-S protein, b) a plant is regenerated from a plant cell obtained in step a) and c) if necessary, further plants are produced from the plants obtained in step b).

The plant cell obtained in step a) may be regenerated to whole plants according to methods known to the skilled person, as for example using the methods described in "plant Cell Culture Protocols" 1999, edited by R. D. Hall, Humana Press, ISBN 0-89603-549-2.

In a preferred method for the manufacture of genetically modified plant of the invention the nucleic acid molecule encoding the dextransucrase DSR-S protein in step a) is translationally fused with a nucleic acid molecule encoding a plastidic signal sequence.

The production of further plants according to Step (c) of the method according to the invention can be carried out, for example, by vegetative propagation (for example using cuttings, tubers or by means of callus culture and regeneration of whole plants) or by sexual propagation. Here, sexual propagation preferably takes place under controlled conditions, i.e. selected plants with particular characteristics are crossed and propagated with one another.

The present invention also relates to a method for the manufacture of a genetically modified plant according to the method disclosed above, wherein the nucleic acid molecule encoding a dextransucrase DSR-S protein is integrated into the plastidial genome of the plant.

The nucleic acid molecule encoding a dextransucrase DSR-S protein may be from any desired origin, preferrably the nucleic acid molecule encoding a dextransucrase originates form bacteria expressing such proteins.

More preferably, nucleic acid molecules used in the invention may encode a dextransucrase DSR-S protein from a bacteria selected from the group consisting of *Leuconostoc*, *Lactobacillus* and *Streptococcus* bacteria.

Most preferably, nucleic acid molecules used in the invention may encode a dextransucrase DSR-S protein from *Leuconostoc mesenteroides*, especially preferrably from *Leuconostoc mesenteroides* strain NRRL B512F.

Nucleic acid molecules encoding a dextransucrase DSR-S protein used in the invention may be isolated e.g. from genomic DNA or DNA libraries produced from any origin, preferably from bacteria. Alternatively, they may have been produced by means of recombinant DNA techniques (e.g. PCR) or by means of chemical synthesis. The identification and isolation of such nucleic acid molecules may take place by using the molecules according to the invention or parts of these molecules or, as the case may be, the reverse complement strands of these molecules, e.g. by hybridization according to standard methods (see e.g. Sambrook et al., 1989, Molecular Cloning, A Laboratory Manual, 2nd Edition, Cold Spring Harbor Laboratory Press, Cold Spring Harbor, N.Y.).

As a probe for hybridization e.g. nucleic acid molecules may be used which exactly or basically contain the nucleotide sequences indicated under SEQ ID No. 1 or parts thereof. The fragments used as hybridization probe may also be synthetic fragments which were produced by means of the conventional synthesizing methods and the sequence of which is basically identical with that of a nucleic acid molecule according to the invention.

The molecules hybridizing to the nucleic acid molecules used in the invention also comprise fragments, derivatives and allelic variants of the above-described nucleic acid molecules which encode a dextransucrase DSR-S protein. In this context, fragments are defined as parts of the nucleic acid molecules, which are long enough in order to encode proteins. In this context, the term derivatives means that the sequences of these molecules differ from the sequences of the above-mentioned nucleic acid molecules at one or more positions and that they exhibit a high degree of homology to these sequences. Homology means a sequence identity of at least 70% and still more preferably a sequence identity of more than 90% and most preferably a sequence identity of more than 95%. The deviations occurring when comparing with the above-described nucleic acid molecules might have been caused by deletion, substitution, insertion or recombination.

Moreover, homology means that functional and/or structural equivalence exists between the respective nucleic acid molecules or the proteins they encode. The nucleic acid molecules, which are homologous to the above-described molecules and represent derivatives of these molecules, are generally variations of these molecules, that constitute modifications which exert the same biological function: These variations may be naturally occurring variations, for example sequences derived from other bacteria, or mutations, whereby these mutations may have occurred naturally or they may have been introduced by means of a specific mutagenesis. Moreover the variations may be synthetically produced sequences. The allelic variants may be naturally occurring as well as synthetically produced variants or variants produced by recombinant DNA techniques.

In a preferred embodiment of the present invention the nucleic acid molecules encoding a dextransucrase DSR-S protein is chosen from the group consisting of:
a) Nucleic acid molecules, which encode a protein with the amino acid sequence given under Seq ID NO: 2 or SEQ ID NO: 4;
b) Nucleic acid molecules, which encode a protein, the amino acid sequence of which has an identity of at least 70% with the amino acid sequence given under SEQ ID NO: 2 or SEQ ID NO: 4;
c) Nucleic acid molecules, comprising the nucleotide sequence shown under SEQ ID NO: 3 or a complementary sequence thereof;
d) Nucleic acid molecules, the nucleic acid sequence of which has an identity of at least 70% with the nucleic acid sequences described under a) or e);
e) Nucleic acid molecules, the nucleotide sequence of which deviates from the sequence of the nucleic acid molecules identified under a), b), c) or d) due to the degeneration of the genetic code; and
f) Nucleic acid molecules, which represent fragments, allelic variants and/or derivatives of the nucleic acid molecules identified under a), b), c), d) or e).

In a further preferred embodiment of the invention, the nucleic acid molecules encoding a dextransucrase protein DSR-S encode a protein, the amino acid sequence of which has an identity of at least 70%, preferably at least 80%, more preferably at least 90%, and still more preferably at least 95% to the sequence Seq ID N0: 2 or SEQ ID N0:4.

In an other further preferred embodiment, the nucleic acid molecule encoding a dextransucrase protein DSR-S has a nucleic acid sequence with an identity of at least 70%, preferably at least 80%, more preferably at least 90%, and still more preferably at least 95% to the sequence Seq ID N0:1 or SEQ ID N0: 3.

In conjunction with the present invention, the term "identity" is to be understood to mean the number of amino acids/nucleotides corresponding with the amino acids/nucleotides of other protein/nucleic acid, expressed as a percentage. Identity is preferably determined by comparing the Seq. ID NO: 1, SEQ ID NO: 2, Seq. ID NO: 3 or SEQ ID NO: 4 with other protein/nucleic acid with the help of computer programs. If sequences that are compared with one another have different lengths, the identity is to be determined in such a way that the number of amino acids, which have the shorter sequence in common with the longer sequence, determines the percentage quotient of the identity. Preferably, identity is determined by means of the computer program ClustalW, which is well known and available to the public (Thompson et al., Nucleic Acids Research 22 (1994), 4673-4680). ClustalW is made publicly available by Julie Thompson (Thompson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW can also be downloaded from different Internet sites, including the IGBMC (Institut de Génétique et de Biologie Moléculaire et Cellulaire, B.P.163, 67404 Illkirch Cedex, France; ftp://ftp-igbmc.u-strasbg.fr/pub/) and the EBI (ftp://ftp.ebi.ac.uk/pub/software/) as well as from all mirrored Internet sites of the EBI (European Bioinformatics Institute, Wellcome Trust Genome Campus, Hinxton, Cambridge CB10 1SD, UK).

Preferably, Version 1.8 of the ClustalW computer program is used to determine the identity between proteins according to the invention and other proteins. In doing so, the following parameters must be set:
KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

Preferably, Version 1.8 of the ClustalW computer program is used to determine the identity between the nucleotide sequence of the nucleic acid molecules according to the invention, for example, and the nucleotide sequence of other nucleic acid molecules. In doing so, the following parameters must be set:
KTUPLE=2, TOPDIAGS=4, PAIRGAP=5, DNAMATRIX: IUB, GAPOPEN=10, GAPEXT=5, MAXDIV=40, TRANSITIONS: unweighted.

Furthermore, identity means that functional and/or structural equivalence exists between the nucleic acid molecules concerned or the proteins coded by them. The nucleic acid molecules, which are homologous to the molecules described above and constitute derivatives of these molecules, are generally variations of these molecules, which constitute modifications, which execute the same biological function. At the same time, the variations can occur naturally, for example they can be sequences from other bacterial species, or they can be mutations, wherein these mutations may have occurred in a natural manner or have been introduced by objective mutagenesis. The variations can also be synthetically manufactured sequences. The allelic variants can be both naturally occurring variants and also synthetically manufactured variants or variants produced by recombinant DNA techniques. Nucleic acid molecules, which deviate from nucleic acid molecules according to the invention due to degeneration of the genetic code, constitute a special form of derivatives.

The use of nucleic acid molecules that encode a dextransucrase DSR-S protein and the sequence of which differs from the nucleotide sequences of the above-mentioned molecules due to the degeneracy of the genetic code are also the subject-matter of the invention.

The invention also relates to the use of nucleic acid molecules showing a sequence which is complementary to the whole or to a part of one of the above-mentioned sequences.

For expressing nucleic acid molecules described above, these are preferably linked with regulatory DNA sequences, which guarantee initiation of transcription in plant cells. In particular, these include promoters. In general, any promoter that is active in plant cells is eligible for expression.

At the same time, the promoter can be chosen so that expression takes place constitutively or only in a certain tissue, at a certain stage of the plant development or at a time determined by external influences. The promoter can be homologous or heterologous both with respect to the plant and with respect to the nucleic acid molecule.

Suitable promoters are, for example, the promoter of the 35S RNA of the cauliflower mosaic virus and the ubiquitin promoter from maize for constitutive expression, the patatin promoter B33 (Rocha-Sosa et al., EMBO J. 8 (1989), 23-29) for tuber-specific expression in potatoes or a promoter, which only ensures expression in photosynthetically active tissues, e.g. the ST-LS1 promoter (Stockhaus et al., Proc. Natl. Acad. Sci. USA 84 (1987), 7943-7947; Stockhaus et al., EMBO J. 8 (1989), 2445-2451) or, for endosperm-specific expression of the HMG promoter from wheat, the USP promoter, the phaseolin promoter, promoters of zein genes from maize (Pedersen et al., Cell 29 (1982), 1015-1026; Quatroccio et al., Plant Mol. Biol. 15 (1990), 81-93), glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218) or shrunken-1 promoter (Werr et al., EMBO J. 4 (1985), 1373-1380). However, promoters can also be used, which are only activated at a time determined by external influences (see for example WO 9307279). Promoters of heat-shock proteins, which allow simple induction, can be of particular interest here. Furthermore, seed-specific promoters can be used, such as the USP promoter from *Vicia faba*, which guarantees seed-specific expression in *Vicia faba* and other plants (Fiedler et al., Plant Mol. Biol. 22 (1993), 669-679; Bäumlein et al., Mol. Gen. Genet. 225 (1991), 459-467).

Promoters which are active in plastids of plant cells may be used if the nucleic acid construct of the invention is integrated in the plastidial genome of the plant cell. Among the promoters active in plastids of plant cells, by way of example, special mention can be made of the psbA gene which encodes the D1 polypeptide of PSII (Staub et al. 1993 EMBO Journal 12(2): 601-606), and the constitutive Prrn promoter which regulates the ribosomal RNA operon (Staub et al. 1992 Plant Cell 4:39-45).

Furthermore, a termination sequence (polyadenylation signal) can be present, which is used for adding a poly-A tail to the transcript. A function in the stabilisation of the transcripts is ascribed to the poly-A tail. Elements of this type are described in the literature (cf. Gielen et al., EMBO J. 8 (1989), 23-29) and can be exchanged at will.

Plants obtainable by the method of the invention for the manufacture of a plant according to the invention are a further embodiment of the invention.

Furthermore, the invention relates to vectors, especially plasmids, cosmids, viruses, bacteriophages and other vectors common in genetic engineering, which contain the above-mentioned nucleic acid molecules encoding a dextransucrase DSR-S protein. Such vectors are preferably vectors which can be used for the transformation of plant cells. More preferably, they allow for the integration of the nucleic acid molecules of the invention into the nuclear or plastidial genome of the plant cell, if necessary in combination with flanking regulatory regions. Examples are binary vectors which may be used in the *Agrobacterium*-mediated gene transfer, as for example pBIN20 binary vector (Hennegan and Danna, 1998). Examples of vectors which may be used for direct plastid transformation are given in WO 04/055191.

The plasmid comprising the heterologous nucleic acid to be introduced into the plant further will generally contain either a selectable marker or a reporter gene or both to facilitate identification and selection of transformed cells. Alternatively, the selectable marker may be carried on a separate vector and used in a co-transformation procedure. Both selectable markers and reporter genes may be flanked with appropriate regulatory sequences to enable expression in plants. Useful selectable markers and reporter genes are well known in the art and include, for example, antibiotic and herbicide resistance genes, genes encoding beta-glucuronidase enzyme (Staub et al, 1993) or green fluorescent protein (Sidorov et al, 1999).

Specific examples of such genes are disclosed in Weising et al, 1988, Svab et al 1993, White et al., Nucleic Acid Res. 18(4):1062.

By using the nucleic acid molecule encoding a dextransucrase DSR-S protein, it is now possible—by means of recombinant DNA techniques—to interfere with the starch metabolism of plant cells or plants in a way so far impossible. Thereby, the starch metabolism may be modified in such a way that a modified starch is synthesized which e.g. is modified, compared to the starch synthesized in corresponding non-genetically modified wild type plant cells or non-genetically modified wild type plants, respectively, in its physico-chemical properties, the pastification behavior, the size and/or the shape of the starch granule. Compared with wild-type starch, such starch may be modified in particular with respect to its viscosity and/or the gel formation properties of the glues of this starch and/or its capability to be digested.

The present invention therefore also relates to modified starches obtainable from plant cells according to the invention or plants according to the invention, from propagation material according to the invention or from harvestable plant parts according to the invention.

In a particularly preferred embodiment, the present invention relates to modified potato starch.

The present invention further relates to a method for the manufacture of a modified starch comprising the step of extracting the starch from a plant cell according to the invention, from a plant according to the invention, from harvestable parts of a plant according to the invention, or from a plant obtainable by means of a method of the invention for the manufacture of a plant according to the invention.

Preferably, such a method also comprises the step of harvesting the cultivated plants and/or starch-storing parts of such plants before extracting the starch. Most preferably, it further comprises the step of cultivating the plants of the invention before harvesting. Methods for the extraction of starch from plants or from starch-storing parts of plants are known to the skilled person. Methods for the extraction of starch from maize seeds have been described e.g. in Eckhoff et al. (Cereal Chem. 73 (1996) 54-57). The extraction of starch on an industrial level is usually achieved by the so-called wet-milling technique. Furthermore, methods for the extraction of starch from various other starch-storing plants have been described, e.g. in "Starch: Chemistry and Technology (Editor: Whistler, BeMiller and Paschall (1994), 2.sup.nd edition, Academic Press Inc. London Ltd; ISBN 0-12-746270-8; see e.g. chapter XII, page 412-468: maize and sorghum starches: production; by Watson; chapter XIII, page 469-479: tapioca, arrowroot and sago starches: production; by Corbishley and Miller; chapter XIV, page 479-490: potato starch: production and use; by Mitch; chapter XV, page 491 to 506: wheat starch: production, modification and use; by Knight and Oson; and chapter XVI, page 507 to 528: rice starch: production and use; by Rohmer and Klem). Appliances generally used for extracting starch from plant material are separators, decanters, hydrocyclones, spray dryers and cyclon driers.

Due to the expression of a nucleic acid molecule encoding a dextransucrase protein, the transgenic plant cells and plants described in the invention synthesize a starch which compared to starch synthesized in corresponding non-genetically modified wildtype plant cells or -genetically modified wild-type plants, respectively, is modified for example in its physico-chemical properties, the pastification behavior, the size and/or the shape of the starch granule. Compared with wildtype-starch, such starch may be modified in particular with respect to its viscosity and/or the gel formation properties of the glues of this starch and/or its capability to be digested.

Thus, also the modified starch obtainable from the method according to the invention is the subject-matter of the present invention.

In a preferred embodiment of the invention the starch of the invention is a native starch.

In conjunction with the present invention, the term "native starch" means that the starch is isolated from plants according to the invention, harvestable plant parts according to the invention or propagation material of plants according to the invention by methods known to the person skilled in the art.

The person skilled in the art knows that the characteristics of starch can be changed by thermal, chemical, enzymatic or mechanical derivation, for example. Derived starches are particularly suitable for different applications in the foodstuffs and/or non-foodstuffs sector. The starches according to the invention are better suited as a starting substance for the manufacture of derived starches than conventional starches.

The present invention therefore also relates to a method for the production of a derived starch, wherein modified starch according to the invention or obtainable by means of a method according to the invention is derived retrospectively.

In conjunction with the present invention, the term "derived starch" is to be understood to mean a modified starch according to the invention, the characteristics of which have been changed after isolation from vegetable cells with the help of chemical, enzymatic, thermal or mechanical methods.

In a preferred embodiment of the present invention, the derived starch according to the invention is starch that has been heat-treated and/or acid-treated.

In a further preferred embodiment, the derived starches are starch ethers, in particular starch alkyl ethers, O-allyl ethers, hydroxylalkyl ethers, O-carboxylmethyl ethers, nitrogen-containing starch ethers, phosphate-containing starch ethers or sulphur-containing starch ethers.

In a further preferred embodiment, the derived starches are cross-linked starches.

In a further preferred embodiment, the derived starches are starch graft polymers.

In a further preferred embodiment, the derived starches are oxidised starches.

In a further preferred embodiment, the derived starches are starch esters, in particular starch esters, which have been introduced into the starch using organic acids. Particularly preferably these are phosphate, nitrate, sulphate, xanthate, acetate or citrate starches.

Methods for manufacturing derived starches according to the invention are known to the person skilled in the art and are adequately described in the general literature. An overview on the manufacture of derived starches can be found, for example, in Orthoefer (in Corn, Chemistry and Technology, 1987, eds. Watson und Ramstad, Chapter 16, 479-499).

Derived starch obtainable by the method according to the invention for manufacturing a derived starch is also the subject matter of the present invention.

A further embodiment of the invention is the use of modified starch according to the invention for the production of a derived starch.

The invention also relates to the use of a plant cell according to the invention, a plant according to the invention, harvestable parts of a plant according to the invention or a plant obtainable by means of a method of the invention, for the production of a modified starch.

The invention also relates to the use of a nucleic acid molecule encoding a dextransucrase DSR-S protein for the manufacture of a genetically modified plant cell according to the invention, a genetically modified plant according to the invention, propagation material according to the invention, or harvestable parts of plants according to the invention.

Furthermore the use of a nucleic acid sequence encoding a dextransucrase DSR-S protein for the production of a modified starch according to the invention is an embodiment of the invention.

General Methods

Method 1: Determination of the Viscosity Characteristics by Means of a Rapid Visco Analyser (RVA).

3 g of sample (for example flour) are taken up in 25 ml of $H_2O$ (VE-type water, conductivity of at least 15 mega ohm) and used for the analysis in a Rapid Visco Analyser Super3 (Newport Scientific Pty Ltd., Investment Support Group, Warriewod NSW 2102, Australia). The apparatus is operated following the manufacturer's instructions. The viscosity values are indicated in Centipoise (cP) in accordance with the manufacturer's operating manual, which is incorporated into the description herewith by reference. To determine the viscosity of the aqueous starch solution, the starch suspension is first stirred for 10 seconds at 960 rpm and subsequently heated at 50° C. at a stirring speed of 160 rpm, initially for a minute (step 1). The temperature was then raised from 50° C. to 95° C. at a heating rate of 12° C. per minute (step 2). The temperature is held for 2.5 minutes at 95° C. (step 3) and then cooled from 95° C. to 50° C. at 12° C. per minute (step 4). In the last step (step 5), the temperature of 50° C. is held for 2 minutes. The viscosity is determined during the entire duration.

After the program has ended, the stirrer is removed and the beaker covered. The gelatinized starch is now available for the texture analysis after 24 hours incubation at room temperature.

The profile of the RVA analysis contains parameters which are shown for the comparison of different measurements and substances. In the context of the present invention, the following terms are to be understood as follows:

1. Maximum Viscosity (RVA Max)

The maximum viscosity is understood as meaning the highest viscosity value, measured in cP, obtained in step 2 or 3 of the temperature profile.

2. Minimum Viscosity (RVA Min)

The minimum viscosity is understood as meaning the lowest viscosity value, measured in cP, observed in the temperature profile after the maximum viscosity. Normally, this takes place in step 3 of the temperature profile.

3. Final Viscosity (RVA Fin)

The final viscosity (or end viscosity) is understood as meaning the viscosity value, measured in cP, observed at the end of the measurement.

4. Setback (RVA Set)

What is known as the "setback" is calculated by subtracting the value of the final viscosity from that of the minimum occurring after the maximum viscosity in the curve.

5. Gelatinization Temperature (RVA PT)

The gelatinization temperature is understood as meaning the point in time of the temperature profile where, for the first time, the viscosity increases drastically for a brief period.

Method 2: Determination of the Viscometric Profiles by Means of a Thermo Haake Rheoscope.

Viscometric profiles from a 2% starch suspension were determined by applying a small oscillating shear deformation at a frequency of 1 Hz, using a Thermo Haake rheoscope. The rheometer was equipped with parallel plate geometry (typ C70/1 Ti) and the gap size was 0.1 mm. The pasting profile of the 2% starch-water (w/v) suspension was obtained by heating the suspension from 40° C. to 90° C. at a rate of 2° C./min, where it was kept for 15 min followed by cooling to 20° C. at a rate of 2° C./min and hold again for 15 min at 20° C. The Tg (start gelatinization temperature), Tp (peak temperature) and viscosities were measured. Subsequently, from the retrogradated sample, an amplitude sweep was run at 10 Pa increasing to 1.000 Pa within 60 s to check that the measurements were made in the linear region, in which the amplitudes of stress and strain are proportional to each other.

Method 3: Determination of the Gel Formation Properties of the Glues of the Starch by Means of a Texture Analyser TA-XT2.

The sample is gelatinized in the RVA apparatus in an aqueous suspension by means of a Rapid Visco Analyser (RVA) and subsequently stored for 24 hours at room temperature in a sealed container. The samples are fixed under the probe (round piston with planar surface) of a Texture Analyser TA-XT2 from Stable Micro Systems (Surrey, UK) and the gel strength was determined using the following parameters:

| Test speed | 0.5 mm/s |
|---|---|
| Depth of penetration | 7 mm |
| Contact surface | 113 mm2 |
| Pressure | 2 g. |

Method 4: Determination of Digestibility of Starch Based on the Determination of Resistant Starches RS Type III.

Resistant starches, RS, can be divided into the following types:

| RS type 1 | Starch not accessible physically to digestion, for example partly milled plant cells (e.g. in muesli). |
|---|---|
| RS type 2 | Indigestible granular starch (starch grains), for example from raw potatoes, green bananas, etc. |
| RS type 3 | Indigestible retrograded starch that is obtained, for example, by thermal and/or enzymatic treatment and then retrograded. |
| RS type 4 | Indigestible, chemically modified starch that is formed, for example, by cross-bonding or esterification (acetylation, etc). |

The determination of resistant starches RS Type III was obtained using the following steps:

a) Pancreatine/Amyloglucosidase (AGS) Treatment

Pancreatine/amyloglucosidase digestion buffer used:
0.1 M Na acetate pH 5.2
4 mM CaCl2

Preparation of the Enzyme Solution:

12 g pancreatine (Merck, Product no. 1.07130.1000) were stirred in 80 ml demineralised water (conductivity ca. 18 M ohm) for 10 min at 37° C. and then centrifuged for 10 min at 3000 rpm.

54 ml of the supernatant obtained after centrifugation were treated with 9.86 ml demineralised water and 0.14 ml amyloglucosidase (6000 u/ml, Sigma, Product no. A-3042).

Pancreatine/Amyloglucosidase (AGS) Digestion Procedure 5 assays of the pancreatine/amyloglucosidase (AGS) digestion are prepared each time for each batch starch to be measured. No enzyme solution is later added to 2 of each of these 5 assays. The assays to which no enzyme solution is added are designated as reference and are used for determination of the recovery rate. The remaining 3 assays are designated as sample, later treated with enzyme solution and used for the determination of the RS content.

A number of reaction vessels which contain no starch were processed in parallel (blank samples). These blank samples which contain no starch are used for the determination amount of co-precipitated material (protein, salts).

The tare weight of 50 ml reaction vessels (Falcon tubes) was determined and then in each case ca. 200 mg of the starch are weighed in.

15 ml Na acetate buffer was added to each of the linear water-insoluble poly-alpha-1,4-D-glucan samples and the blanks samples, and 20 ml Na acetate buffer to each of the references (see above). These samples were pre-warmed to 37° C.

The reaction was initiated by the addition of 5 ml enzyme solution to each of the individual reaction vessels of the samples and the blank samples which were then shaken for 2 hours at 37° C. (200 rpm).

The reaction was quenched by the addition of 5 ml glacial acetic acid (equilibrated to pH 3.0) and 80 ml technical ethanol to the samples, blank samples and the references.

Precipitation of the starch from the reaction mixture was achieved by incubation of the quenched reaction assay at room temperature for 1 hour. After sedimentation (centrifugation for 10 min at 2500×g) the sediment of the individual assays obtained was washed twice with 80% ethanol to remove short-chain glucans and then freeze dried after cooling to −70° C. The samples were re-weighed and the weight differences used for the calculation of the "gravimetric" RS content.

b) Determination of the RS Content

The following procedure was used for the determination of RS content of the individual batches of water-insoluble starch:

a) Determination of the water content of the individual sample batches of starch (wt.H2O)
b) Determination of the tare weight of the individual reaction vessels for the respective samples (wt.RGP), references (wt.RGR) and the blank samples (wt.RGB).
c) Weighing ca. 200 mg of water-insoluble starch into the individual reaction vessels for samples (wt.P) and references (wt.R)
d) Calculation of the dry fraction of the weights for samples (wt.Ptr=wt.P−wt.H2O) and references (wt Rtr=wt.P−wt.H2O)
e) Enzymatic digestion of the respective samples and blank samples. References are treated in the same way but without addition of the enzyme solution.
f) Precipitation, sedimentation, washing and freeze drying of the substances remaining in the reaction vessels of the samples, references and blank samples after the treatment described in e).
g) Weighing of the substances remaining in the reaction vessels of the samples (wt.PRG), references (wt.RRG) and blank samples (wt.BRG), inclusive of reaction vessel after the treatment described in f).
h) Calculation of the weight of the substances remaining in the reaction vessels of the
samples (wt.Pnv=wt.PRG−wt.RGP),
references (wt.Rnv=wt.RRG−wt.RGR)
and the blank samples (wt.Bnv=wt.BRG−wt.RGB)
after the treatment described under f).
i) Determination of the water content of the substances remaining in the reaction vessels of
samples (wt.H2OPnv),
references (wt.H2ORnv)
and the blank samples (wt.H2OBnv)
after the treatment described under f).
j) Calculation of the dry fraction of the substances remaining in the reaction vessels of the
samples (wt.Pnvtr=wt.Pnv−wt.H2OPnv)
references (wt.Rnvtr=wt.Rnv−wt.H2ORnv)
and the blank samples (wt.Bnvtr=wt.Bnv−H2OBnv)
after the treatment described under f).
k) Determination of the corrected weights for the samples (wt.Pnvkorr=wt.Pnvtr−wt.Bnvtr)
and references (wt.Rnvkorr=wt.Rnvtr−wt.Bnvtr)
l) Calculation of the percentage fraction of the corrected weights of the water-insoluble starch remaining after enzymatic digestion relative to the dry weight of the starting amount of the
samples (RSaP=wt.Pnvkorr/wt.Ptr×100)
and calculation of the percentage fraction of the corrected weights of the remaining water-insoluble starch of the references relative to the dry weight of the starting amounts of the references (RSaR=wt.Rnvkorr/wt.Rtr×100).
m) Determination of the mean value of the percentage fractions of the water-insoluble starch remaining after enzymatic digestion of the samples (RSaPMW=n×RSaP/n)
and determination of the mean values of the percentage fractions of the remaining water-insoluble starch of the references: (recovery rate; RSaRMW=n×RSaR/n)
where n is the number of sample and reference assays carried out for the respective batches of water-insoluble starch.
n) Determination of the percentage RS content of the individual batches of water-insoluble starch by correction of the mean values of the percentage fractions of the water-insoluble starch remaining after enzymatic digestion with the recovery rate (RS=RSaPMW/RSaRMW×100).

The invention is specifically illustrated by the following examples which are not in any way limiting.

EXAMPLE 1

Cloning of a Mature Gene Encoding a Dextransucrase from *L. mesenteroides*.

An expression cassette containing the patatin promoter (Wenzler et al., 1989), the chloroplastic ferredoxin transit peptide (FD) from *Silene pratensis* (Smeekens et al., 1985; Pilon et al., 1995) fused to the NOS terminator was cloned into the pBluescript SK (pBS SK) plasmid, resulting in pPF.

In order to isolate nucleic acid molecules encoding a dextransucrase, a mature DsrS gene was amplified by PCR from the genomic DNA from *L. mesenteroides* NRRL B-512 F (WO 89/12386), with a forward primer containing a SmaI restriction site (5'-GCCTCATTTGCTCCCGGGACAC-CAAGT-3') (SEQ ID NO: 5) and a reverse primer containing a NruI restriction site (5'-TGGTGGTTCGCGAGTTATGCT-GACACA-3') (SEQ ID NO: 6) using the proofreading Pfu turbo DNA polymerase (2.5 units/μl; Stratagene, UK) and cloned into the SmaI/EcoRV restriction sites of pPF between FD and the NOS terminator, resulting in pPFDsrS. pPFDsrS was digested with SacI and KpnI and ligated into a pBIN20 binary vector (Hennegan and Danna, 1998), resulting in pBinDsrS. pBinDsrS is shown in FIG. 1.

EXAMPLE 2

Transformation of Potato Plants pBinDsrS was transformed into *Agrobacterium tumefaciens* strain LBA 4404 using electroporation (Takken et al., 2000). Internodal stem segments from two tetraploid potato cultivars (cv. Kardal (KD) and amylose-free (amf) mutant) were used for *Agrobacterium*-mediated transformation. Transformants were selected on plates with MS30 medium (Murashige and Skoog, 1962) containing kanamycin (100 mg/l). 30 transgenic, root forming, shoots were multiplied and were transferred to the greenhouse for tuber development. The mature tubers were harvested after 18 weeks.

EXAMPLE 3

Starch Isolation and Immunological Detection, of Dextrans in Tuber Juices and Gelatinized Starches Potato tubers were peeled and homogenized in a Sanamat Rotor (Spangenberg, The Netherlands). The resulting homogenate was allowed to settle overnight at 4° C. and the potato juice was decanted and stored at −20° C. for characterization of soluble dextran polymers. The starch pellet was washed three times with water and finally air-dried at room temperature for at least three days. The dried starch was powdered and stored at room temperature.

Presence of dextrans was investigated with enzyme-linked immunosorbent assay (ELISA) as described by Matsuda and Kabat (1989) by using monoclonal α-(1,6) dextran antibodies (4.3F1 (groove-type) and 16.4.12E (cavity-type)) (Wang et al., 2002).

ELISA analyses show that dextran polymers were detected both in transgenic potato lines obtained from Kardal lines or amylose-free mutant, then no dextran was detected in wild-type kardal lines or non-transgenic amylose-free mutant.

EXAMPLE 4

Impact of Dextran Expression on Starch Granule Morphology, Plant Morphology, Tuber Number and Yield Analysis of starch granule morphology was performed by light microscopy (LM) (Axiophot, Germany) equipped with a Sony colour video camera (CCD-Iris/RGB) and scanning electron microscopy (SEM, JEOL 6300F, Japan). For LM, the granules were stained with a 2× diluted Lugol solution before visualisation.

Impact of dextran expression was scored by analyzing a population of 100 starch granules per selected transformants in triplicates compared to starch granules isolates from wildtype lines.

Both technology show a modified starch granule morphology for starch isolated from transgenic lines expressing dextran. The granules of these transformants exhibited irregular surfaces, and round-protruded structures in comparison to starch granules isolated from wildtype lines.

Figure 2:
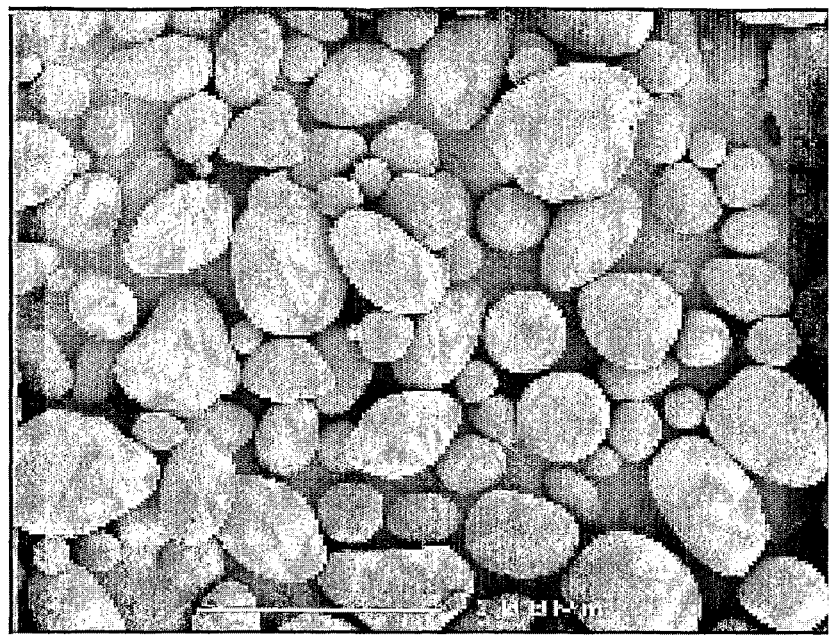
FIG. 2: Modified starch granule morphology observed by scanning electron microscopy analysis performed on the starch of a selected transformant (dsrS30) (B), compared to the starch of a wild-type Kardal plant (Kardal) (A)
Figure 2:
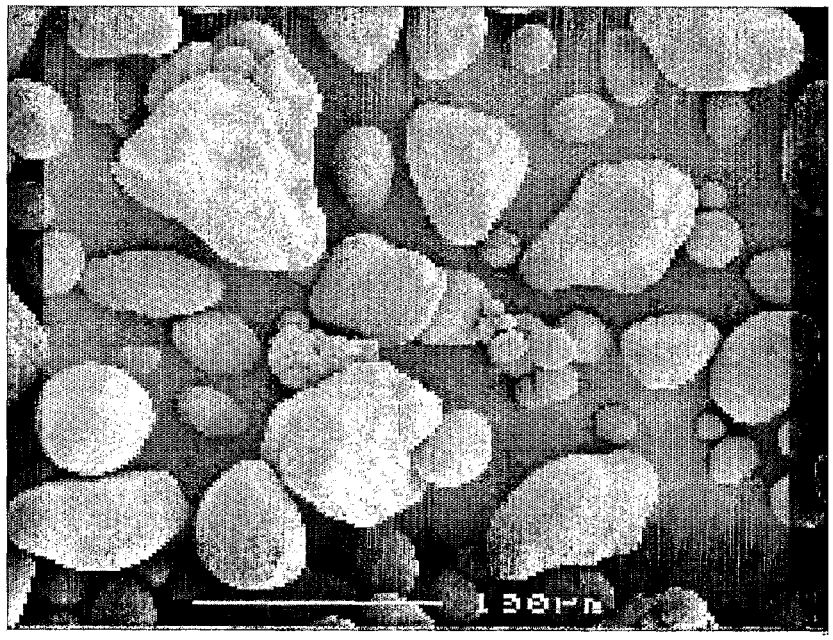

FIG. 2 shows the modified starch granule morphology observed by scanning electron microscopy analysis performed on the starch of a selected transformant (dsrS30), compared to the starch of a wild-type Kardal plant (Kardal)

On an other hand, the morphology of plant expressing dextran showed no phenotypic alteration in comparison to KD wildtype plants. In addition, there was no correlation between the expression of dextran polymers and alteration of tuber number and yield.

EXAMPLE 5

Impact of Dextran Expression on Digestibility of Starch

The digestibility of starch has been determined using the method detailed in the general methods (method 4). The determination was based upon the method of Englyst (European Journal of Clinical Nutrition (1992) 46 (suppl. 2), p. 33-50) for the determination of resistant starches Type III, modified in correspondence with the information on the determination of RS content in WO 00 02926.

The following table show a significant increase in the percentage of the digested starch for the sample extracted from a selected transformant (DsrS30) compared to the starch of a wild-type Kardal plant (Kardal).

| Results: Percentage of digested starch (%): | | | | | | | | | |
|---|---|---|---|---|---|---|---|---|---|
| | min | | | | | | | | |
| | 15 | 30 | 45 | 60 | 120 | 180 | 240 | 300 | 360 |
| Kardal | 3 | 4 | 5 | 7 | 13 | 20 | 27 | 33 | 38 |
| DsrS30 | 3 | 5 | 7 | 8 | 15 | 23 | 31 | 37 | 44 |

Kardal: average values from four independent measurements
DsrS30: average values from two independent measurements

EXAMPLE 6

Impact of Dextran Expression on Viscosity of Starch

The viscometric profiles from a starch suspension obtained from a transformant (DsrS30) and from a wild-type Kardal plant (Kardal) have been selected by the mean of a Thermo Haake rheoscope, using the method described in the general methods (method 2).

The following table show a significant decrease in the final viscosity for the sample extracted from a selected transformant (DsrS30) compared to the starch of a wild-type Kardal plant (Kardal).

| | Kardal and DSrS 30: average values of two independent analyses, from a 2% starch solutions | | | | |
|---|---|---|---|---|---|
| Starch Sample | T-Onset (° C.) | T-Peak (° C.) | Peak Viscosity (PaS) | Valley Viscosity (PaS) | End Viscosity (PaS) |
| Kardal | 75.7 | 78.1 | 122 | 27 | 134 |
| DsrS30 | 73.8 | 75.9 | 135.5 | 22.5 | 93 |

REFERENCES

An et al. EMBO J. 4, (1985), 277-287
Bäumlein et al., Mol. Gen. Genet. 225 (1991), 459-467
Chan et al., Plant Mol. Biol. 22, (1993), 491-506;
van Cleve, J. W., Schaefer, W. C. and Rist, C. E. 1956. J. Am. Chem. Soc. 78: 4435-4438.
Conner and Domisse, Int. J. Plant Sci. 153 (1992), 550-555
Creissen et al., Plant J. 8 (1995), 167-175
De Vuyst and Degeest 1999 FEMS Microbiol Rev. 23 (2):153-77.

Deng et al, Science in China 33, (1990), 28-34
Eckhoff et al. Cereal Chem. 73 (1996) 54-57
Emanuelsson O. et al, 1999, Protein Science: 8:978-984
Englyst H. N. et al., European Journal of Clinical Nutrition 4, Suppl. 2, S33-S50
Fiedler et al., Plant Mol. Biol. 22 (1993), 669-679
Fraley et al., Crit. Rev. Plant Sci. 4, 1-46
Fromm et al., Biotechnology 8, (1990), 833-844;
Fu D, Robyt J F (1990) Arch Biochem Biophys 283: 379-387
Gallardo et al. (1995), Planta 197, 324-332
Gerrits, N., Turk, S. C. H. J., van Dun, K. P. M., Hulleman, S. H. D., Visser, R. G. F., Weisbeek, P. J. and Smeekens, S. C. M. 2001. Plant Physiol. 125: 926-934.
Gielen et al. 1989, EMBO J. 8, 23-29
Gordon-Kamm et al. 1990, Plant Cell 2, 603-618;
Hiei et al. (1994), Plant J. 6, 271-282
Hehre E J, Hamilton D M, Carlson A S (1949). J Biol Chem 177: 267-279
Hennegan, K. P. and Danna, K. J. (1998). Plant Mol. Biol. Rep. 16:129-131.
Hoekema, I N: The Binary Plant Vector System Offsetdrukkerij Kanters B. V., Alblasserdam (1985), Chapter V
Janecek S, Svensson B, Russell R R B (2000). FEMS Microbiol Left 192: 53-57
Jeanes, A., Haynes, W. C., Wilham, C. A., Rankin, J. C., Melvin, E. H., Austin, M. J., Cluskey, J. E., Fisher, B. E., Tsuchiya, H. M. and Rist, C. E. (1954). J. Am. Chem. Soc. 76: 5041-5052.
Khan M. S. and Maliga P. (1999). Nat. Biotechnol. 17, 910-915
Klösgen et al (1989), Mol Gen Genet. 217, 155-161
Kok-Jacob A., Ji Q., Vincken J P., and Visser R G. (2003) J. Plant Physiol; 160, 765-777
Kortstee A J, Vermeesch A M, de Vries B J, Jacobsen E, Visser R G. (1996), Plant J. 10(1):83-90.
Kossmann and Llyod (2000), Crit. Rev. Bioch. Mol. Biol. 35: 141-196
Koziel et al., (1993) Biotechnology 11, 194-200;
Krens et al., Nature 296, (1982), 72-74
Leisy et al., Plant Mol. Biol. 14 (1990), 41-50
MacGregor E A, Jespersen H M, Svensson B (1996). FEBS lett 378: 263-266
Matsuda, T. and Kabat, E. A. 1989. J. Immunol. 142: 863-870.
May et al., Bio/Technology 13, (1995), 486-492;
Monchois V, Remaud-Simeon M, Russell R R B, Monsan P and Willemot R M. 1997. Appl. Microbiol. Biotechnol. 48: 465-472
Monchois V, Remaud-Simeon M, Monsan P and Willemot R M. 1998. FEMS Microbiol. Lett. 159: 307-315
Monchois et al., 1999, FEMS Microbiology Letters 177, 243-248;
Monchois V, Willemot R M and Monsan P. 1999, FEMS Microbiology Reviews 23, 131-151.
Moroc et al., Theor. Appl. Genet. 80, (1990), 721-726).
Murashige, T. and Skoog, F. 1962. Physiol. Plant. 15: 473-497.
Nawrath et al., Proc. Natl. Acad. Sci. 10 USA 91 (1994), 12760-12764)
Nehra et al., Plant J. 5, (1994), 285-297
Oakes J V, Shewmaker C K, Stalker D M (1991). Biotechnol 9: 982-986
Pedersen et al., Cell 29 (1982), 1015-1026;
Pilon, M., Wienk, H., Sips, W., de Swaaf, M., Talboom, I., van't H of, R., de Korte-Kool, G., Demel, R., Weisbeek, P. and de Kruijff, B. 1995. J. Biol. Chem. 270: 3882-3893.
Quatroccio et al., Plant Mol. Biol. 15 (1990), 81-93
Quirasco et al (Appl. Environ. Microbiol., 65 (12), 5504-5509, 1999
Ritala et al., Plant Mol. Biol. 24, (1994), 317-325;
Ritchie et al, Transgenic Res. 2, (1993), 252-265).
Robyt, J. F. and Walseth, T. F. 1978. Carbohydr. Res. 61: 433-445.
Robyt, J. F. 1995. Adv. Carbohydr. Chem. Biochem. 51: 133-168.
Rocha-Sosa et al., EMBO J. 8, (1989), 29-33
Ruf S., Hermann M., Berger I. J., Carrer H., and Bock R. (2001). Nat. Biotechnol. 19 (9):870-875.
Sambrook et al. (1989, Molecular Cloning: A Laboratory Manual, Nolan C. ed., New York: Cold Spring Harbor Laboratory Press
Shewmaker C K, Boyer C D, Wiesenborn D P, Thompson D B, Boersig M R, Oakes J V, Stalker D M. Plant Physiol. 1994 April; 104(4):1159-66.
Sidebotham, R. L. 1975. Dextrans. Adv. Carbohydr. Chem. Biochem. 30: 371-444.
Sidorov V. A., Kasten D., Pang S. Z., Hajdukiewicz P. T., Staub J. M., and Nehra N. S. (1999). Plant J. 19(2):209-216.
Sikdar S. R., et al. (1998). Plant Cell Reports 18:20-24.
Smeekens, S., van Binsbergen, J. and Weisbeek, P. 1985. Nucleic Acids Res. 13: 3179-3194
Spencer et al., Theor. Appl. Genet. 79, (1990), 625-631)
Staub et al. 1992 Plant Cell 4:39-45
Staub J. M., and Maliga P. (1993). EMBO J. 12 (2): 601-606.
Stockhaus et al., Proc. Natl. Acad. Sci. USA 84 (1987), 7943-7947
Stockhaus et al., EMBO J. 8 (1989), 2445-2451
Su D. and Robyt J F., Arch Biochem Biophys. 1994 Feb. 1; 308(2):471-6.
Svab Z., Hajdukiewicz P., and Maliga P. (1990). Proc. Natl. Acad. Sci. USA 87 (21):8526-8530.
Svab Z., Maliga P. (1993); Proc. Natl. Acad. Sci. USA February 1; 90(3):913-7.
Takken, F. L. W., Luderer, R., Gabriels, S. H. E. J., Westerink, N., Lu, R., de Wit, P. J. G. M. and Joosten, M. H. A. J. 2000. Plant J. 24: 275-283.
Thompson et al., Nucleic Acids Research 22 (1994), 4673-4680
Van Geel-Schutten G H, Faber E J, Smit E, Bonting K, Smith M R, Ten Brink B, Kamerling J P, Vliegenthart J F, Dijkhuizen L., Appl Environ Microbiol. 1999 July; 65(7):3008-14.
Vasil et al., Bio/Technology 11 (1993), 1553-1558;
Wan and Lemaux, Plant Physiol. 104, (1994), 37-48
Wang, D., Liu, S., Trummer, B. J., Deng, C. and Wang, A. 2002. Nature Biotechnol. 20: 275-281.
Weising K, Schell J, Kahl G., Annu Rev Genet. 1988; 22:421-77. Review
Wenzler, H. C., Mignery, A., Fisher, L. M. and Park, W. D. 1989. Plant Mol. Biol. 12: 41-50.
Werr et al., EMBO J. 4 (1985), 1373-1380
Wilmink et al., Plant Cell Reports 11, (1992), 76-80;
White et al., Nucleic Acid Res. 18(4):1062.
Wolter et al, Proc. Natl. Acad. Sci. USA 85 (1988), 846-850
Yoshihara et al., FEBS Lett. 383 (1996), 213-218
Zheng et al., Plant J. 4 (1993), 357-366

The invention claimed is:

1. A genetically modified starch-storing plant cell comprising a nucleic acid molecule encoding a dextransucrase DSR-S protein, wherein said plant cell comprises an enzymatic activity of a dextransucrase DSR-S protein in its plastids, and further wherein said genetically modified plant cell synthesizes a modified starch which has a decreased end viscosity and/or an increased digestibility, in comparison to starch synthesized by corresponding non-genetically modified wild-type plant cells.

2. The genetically modified plant cell of claim 1, wherein the plant cell synthesizes a modified starch which has a decreased end viscosity, in comparison to starch synthesized by corresponding non-genetically modified wild-type plant cells.

3. A plant and/or progeny thereof comprising a genetically modified plant cell of claim 1.

4. The plant and/or progeny thereof of claim 3, which is a potato plant.

5. Propagation material of the plant of claim 3, wherein said propagation material comprises a nucleic acid molecule encoding a dextransucrase DSR-S protein.

6. Harvestable parts of the plant of claim 3, wherein said harvestable plant parts comprise a nucleic acid molecule encoding a dextransucrase DSR-S protein.

7. A method for the manufacture of a genetically modified starch-storing plant, comprising
   a) transforming a starch-storing plant cell with a nucleic acid molecule comprising a nucleic acid molecule encoding a dextransucrase DSR-S protein,
   b) regenerating a plant from the plant cell obtained in step a), and
   c) optionally, producing further plants from the plants obtained in step b),
   wherein said genetically modified plant comprises an enzymatic activity of a dextransucrase DSR-S protein in its plastids, and further wherein said genetically modified plant synthesizes a modified starch which has a decreased end viscosity and/or an increased digestibility, in comparison to starch synthesized by corresponding non-genetically modified wild-type plants.

8. The method of claim 7, wherein the nucleic acid encoding the dextransucrase DSR-S protein in step a) is translationally fused with a nucleic acid molecule encoding a plastidial signal sequence.

9. The method of claim 7, wherein the nucleic acid molecule encoding the dextransucrase DSR-S protein is integrated into the plastidial genome of the plant.

10. The method of claim 7, wherein the nucleic acid molecule encoding a dextransucrase DSR-S protein is
   a) a nucleic acid molecule that encodes a protein comprising the amino acid sequence of SEQ ID NO: 2 or SEQ ID NO: 4;
   b) a nucleic acid molecule that encodes a protein, the amino acid sequence of which has an identity of at least 70% with the amino acid sequence of SEQ ID NO: 2 or SEQ ID NO: 4;
   c) a nucleic acid molecule comprising the nucleotide sequence of SEQ ID NO: 3 or the complementary sequence thereof;
   d) a nucleic acid molecule having an identity of at least 70% with the nucleic acid sequences of a) or e);
   e) a nucleic acid molecule which deviates from the sequence of the nucleic acid molecules of a), b), c), or d) due to the degeneration of the genetic code; or
   f) a nucleic acid molecule comprising a fragment, allelic variant, and/or derivative of the nucleic acid molecules of a), b), c), d), or e).

11. A method for the manufacture of a modified starch comprising the step of extracting the starch from the plant cell of claim 1.

12. A method for the production of a derived starch comprising deriving starch from the plant of claim 3.

13. Propagation material of the plant of claim 4, wherein said propagation material comprises a nucleic acid molecule encoding a dextransucrase DSR-S protein.

14. Harvestable parts of the plant of claim 4, wherein said harvestable plant parts comprise a nucleic acid molecule encoding a dextransucrase DSR-S protein.

15. The plant cell of claim 1, wherein the nucleic acid molecule encoding a dextransucrase DSR-S protein is
   a) a nucleic acid molecule that encodes a protein comprising the amino acid sequence of SEQ ID NO: 2 or SEQ ID NO: 4;
   b) a nucleic acid molecule that encodes a protein, the amino acid sequence of which has an identity of at least 70% with the amino acid sequence of SEQ ID NO: 2 or SEQ ID NO: 4;
   c) a nucleic acid molecule comprising the nucleotide sequence of SEQ ID NO: 3 or the complementary sequence thereof;
   d) a nucleic acid molecule having an identity of at least 70% with the nucleic acid sequences of a) or e);
   e) a nucleic acid molecule which deviates from the sequence of the nucleic acid molecules of a), b), c), or d) due to the degeneration of the genetic code; or
   f) a nucleic acid molecule comprising a fragment, allelic variant, and/or derivative of the nucleic acid molecules of a), b), c), d), or e).

16. The plant of claim 3, wherein the nucleic acid molecule encoding a dextransucrase DSR-S protein is
   a) a nucleic acid molecule that encodes a protein comprising the amino acid sequence of SEQ ID NO: 2 or SEQ ID NO: 4;
   b) a nucleic acid molecule that encodes a protein, the amino acid sequence of which has an identity of at least 70% with the amino acid sequence of SEQ ID NO: 2 or SEQ ID NO: 4;
   c) a nucleic acid molecule comprising the nucleotide sequence of SEQ ID NO: 3 or the complementary sequence thereof;
   d) a nucleic acid molecule having an identity of at least 70% with the nucleic acid sequences of a) or e);
   e) a nucleic acid molecule which deviates from the sequence of the nucleic acid molecules of a), b), c), or d) due to the degeneration of the genetic code; or
   f) a nucleic acid molecule comprising a fragment, allelic variant, and/or derivative of the nucleic acid molecules of a), b), c), d), or e).

17. The plant cell of claim 15, wherein the nucleic acid molecule encodes a protein comprising the amino acid sequence of SEQ ID NO: 2 or SEQ ID NO: 4.

18. The plant cell of claim 15, wherein the nucleic acid molecule encodes a protein comprising an amino acid sequence of which has an identity of at least 90% with the amino acid sequence of SEQ ID NO: 2 or SEQ ID NO: 4.

19. The plant cell of claim 15, wherein the nucleic acid molecule comprises the nucleotide sequence of SEQ ID NO: 3 or the complementary sequence thereof.

20. The plant cell of claim 15, wherein the nucleic acid molecule has an identity of at least 90% with the nucleic acid sequences of a) or e).

21. The plant of claim 16, wherein the nucleic acid molecule encodes a protein comprising the amino acid sequence of SEQ ID NO: 2 or SEQ ID NO: 4.

22. The plant of claim 16, wherein the nucleic acid molecule encodes a protein comprising an amino acid sequence of which has an identity of at least 90% with the amino acid sequence of SEQ ID NO: 2 or SEQ ID NO: 4.

23. The plant of claim 16, wherein the nucleic acid molecule comprises the nucleotide sequence of SEQ ID NO: 3 or the complementary sequence thereof.

24. The plant of claim 16, wherein the nucleic acid molecule has an identity of at least 90% with the nucleic acid sequences of a) or e).

25. The method of claim 10, wherein the nucleic acid molecule encodes a protein comprising the amino acid sequence of SEQ ID NO: 2 or SEQ ID NO: 4.

26. The method of claim 10, wherein the nucleic acid molecule encodes a protein comprising an amino acid sequence of which has an identity of at least 90% with the amino acid sequence of SEQ ID NO: 2 or SEQ ID NO: 4.

27. The method of claim 10, wherein the nucleic acid molecule comprises the nucleotide sequence of SEQ ID NO: 3 or the complementary sequence thereof.

28. The method of claim 10, wherein the nucleic acid molecule has an identity of at least 90% with the nucleic acid sequences of a) or e).

29. The genetically modified plant cell of claim 2, wherein the end viscosity is decreased by at least 15%, in comparison to starch synthesized by corresponding non-genetically modified wild-type plant cells.

30. The genetically modified plant cell of claim 1, wherein the plant cell synthesizes a modified starch which has an increased digestibility, in comparison to starch synthesized by corresponding non-genetically modified wild-type plant cells.

31. The plant of claim 3, wherein the plant synthesizes a modified starch which has a decreased end viscosity, in comparison to starch synthesized by corresponding non-genetically modified wild-type plants.

32. The plant of claim 31, wherein the end viscosity is decreased by at least 15%, in comparison to starch synthesized by corresponding non-genetically modified wild-type plants.

33. The plant of claim 3, wherein the plant synthesizes a modified starch which has an increased digestibility, in comparison to starch synthesized by corresponding non-genetically modified wild-type plants.

34. The method of claim 7, wherein the plant synthesizes a modified starch which has a decreased end viscosity, in comparison to starch synthesized by corresponding non-genetically modified wild-type plants.

35. The method of claim 34, wherein the end viscosity is decreased by at least 15%, in comparison to starch synthesized by corresponding non-genetically modified wild-type plants.

36. The method of claim 7, wherein the plant synthesizes a modified starch which has an increased digestibility, in comparison to starch synthesized by corresponding non-genetically modified wild-type plants.

37. The genetically modified plant cell of claim 30, wherein the digestibility is increased by at least 12%, in comparison to starch synthesized by corresponding non-genetically modified wild-type plant cells.

38. The plant of claim 33, wherein the digestibility is increased by at least 12%, in comparison to starch synthesized by corresponding non-genetically modified wild-type plants.

39. The method of claim 36, wherein the digestibility is increased by at least 12%, in comparison to starch synthesized by corresponding non-genetically modified wild-type plants.

40. The plant cell of claim 1, wherein the nucleic acid molecule encoding a dextransucrase DSR-S protein originates from bacteria expressing such a protein.

41. The plant cell of claim 1, wherein the nucleic acid molecule encoding a dextransucrase DSR-S protein is from *Leuconostoc*, *Lactobacillus*, or *Streptococcus* bacteria.

* * * * *